United States Patent
Wang et al.

(10) Patent No.: US 10,285,659 B2
(45) Date of Patent: May 14, 2019

(54) STORED LUMINESCENCE COMPUTED TOMOGRAPHY

(71) Applicant: Rensselaer Polytechnic Institute, Troy, NY (US)

(72) Inventors: Ge Wang, Loudonville, NY (US); Wenxiang Cong, Albany, NY (US); Chao Wang, Troy, NY (US); Fenglin Liu, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 962 days.

(21) Appl. No.: 14/563,727

(22) Filed: Dec. 8, 2014

(65) Prior Publication Data

US 2015/0157286 A1    Jun. 11, 2015

Related U.S. Application Data

(60) Provisional application No. 61/916,464, filed on Dec. 16, 2013, provisional application No. 61/912,589, filed on Dec. 6, 2013.

(51) Int. Cl.
*A61B 5/00* (2006.01)
*A61B 6/00* (2006.01)
(Continued)

(52) U.S. Cl.
CPC ............ *A61B 6/508* (2013.01); *A61B 5/0073* (2013.01); *A61B 6/032* (2013.01); *A61B 6/485* (2013.01);
(Continued)

(58) Field of Classification Search
CPC .. A61B 6/00; A61B 6/02; A61B 6/032; A61B 6/4007; A61B 6/4028; A61B 6/42; A61B 6/4275; A61B 6/48; A61B 6/481; A61B 6/485; A61B 6/508; A61B 6/52; A61B 5/0073
See application file for complete search history.

(56) References Cited

U.S. PATENT DOCUMENTS

| | | | |
|---|---|---|---|
| 2003/0064532 A1* | 4/2003 | Chen | C09K 11/574 438/3 |
| 2007/0063154 A1* | 3/2007 | Chen | A61B 5/0059 250/483.1 |

(Continued)

OTHER PUBLICATIONS

Uesugi, Kentaro, Akihisa Takeuchi, and Yoshio Suzuki. "Development of micro-tomography system with Fresnel zone plate optics at SPring-8." In Proc. SPIE, vol. 6318, pp. F63181-63181F. 2006.*

(Continued)

*Primary Examiner* — Carolyn A Pehlke
(74) *Attorney, Agent, or Firm* — Murtha Cullina LLP; Anthony P. Gangemi

(57) ABSTRACT

Imaging methods and imaging systems are provided. Methods and systems of the subject invention can include the use of nanoparticles (for example, nanophosphors) within a sample to be imaged. X-ray engraving can be performed and/or X-ray excitation can be used to provide energy to the sample. Stimulation with infrared light, such as near-infrared (NIR) light, and/or optical multiplexing can be used to acquire tomographic data of the sample.

13 Claims, 11 Drawing Sheets
(11 of 11 Drawing Sheet(s) Filed in Color)

(51) Int. Cl.
 A61B 6/03 (2006.01)
 A61B 6/06 (2006.01)
(52) U.S. Cl.
 CPC .............. A61B 5/0071 (2013.01); A61B 6/06
 (2013.01); A61B 6/4035 (2013.01); A61B
 2562/17 (2017.08)

(56) References Cited

U.S. PATENT DOCUMENTS

| | | | | |
|---|---|---|---|---|
| 2007/0218049 A1* | 9/2007 | Chen | ...................... | A61K 33/00 424/130.1 |
| 2009/0086908 A1* | 4/2009 | Harder | ................. | A61B 5/0059 378/62 |
| 2009/0180964 A1* | 7/2009 | Papineni | .............. | A61K 9/0073 424/9.3 |
| 2011/0251484 A1* | 10/2011 | Carpenter | .............. | A61B 6/032 600/431 |

OTHER PUBLICATIONS

Basavaraju, N., S. Sharma, A. Bessière, B. Viana, D. Gourier, and K. R. Priolkar. "Red persistent luminescence in MgGa2O4: Cr3+; a new phosphor for in vivo imaging." Journal of Physics D: Applied Physics 46, No. 37 (2013): 375401.*
Alexandrakis, George et al., "Tomographic bioluminescence imaging by use of a combined optical-PET (OPET) system: a computer simulation feasibility study," Physics in Medicine & Biology, 2005, 50(17):4225-4241.
Alivisatos, Paul. "The use of nanocrystals in biological detection," Nature Biotechnology, 2004, 22(1):47-52.
Arridge, S.R. "A finite element approach for modeling photon transport in tissue," Medical Physics, 1993, 20(2):299-309.
Brannon-Peppas, Lisa et al., "Nanoparticle and targeted systems for cancer therapy," Advanced Drug Delivery Reviews, 2004, 56:1649-1659.
Cai, Xin et al., "Photoacoustic Microscopy in Tissue Engineering," Mater Today (Kidlington), 2013, 16(3):67-77.
Candes, Emmanuel et al., "Robust Uncertainty Principles: Exact Signal Reconstruction from Highly Incomplete Frequency Information," IEEE Transactions on Information Theory, 2006, 52(2):489-509.
Carpenter, C.M. et al., "Hybrid x-ray/optical luminescence imaging: Characterization of experimental conditions," Medical Physics, 2010, 37:4011-4018.
Chen, Dongmei et al., "Cone beam x-ray luminescence computed tomography: A feasibility study," Medical Physics, 2013, 40(3):1-14.
Chen, Jin et al., "Mesh-based Monte Carlo method in time-domain widefield fluorescence molecular tomography," Journal of Biomedical Optics, 2012, 17(10):1-8.
Cong, Alexander et al., "Differential Evolution Approach for Regularized Bioluminescence Tomography," IEEE Transactions on Biomedical Engineering, 2010, 57(9):2229-2238.
Cong, Wenxiang et al., "Practical reconstruction method for bioluminescence tomography," Optics Express, 2005, 13(18):6756-6771.
Cong, Wenxiang et al., "Spectrally resolving and scattering-compensated x-ray luminescence/fluorescence computed tomography," Journal of Biomedical Optics, 2011, 16(6):1-7.
Cong, Wenxiang et al., "X-ray micro-modulated luminescence tomography (XMLT)," Optics Express, 2014, 22(5):5572-5580.
David, C. et at., "Nanofocusing of hard X-ray free electron laser pulses using diamond based Fresnel zone plates," Scientific Reports, 2011, 1(57):1-5.
Donoho, David L. "Compressed Sensing," IEEE Transactions on Information Theory, 2006, 52(4):1289-1306.
Fass, Leonard. "Imaging and cancer: A review," Molecular Oncology, 2008, 2(2):115-152.

Gao, Xiaohu et al., "In vivo cancer targeting and imaging with semiconductor quantum dots," Nature Biotechnology, 2004, 22(8):969-976.
Goy, Alexandre S. et al., "Multiple contrast metrics from the measurements of a digital confocal microscope," Biomedical Optics Express, 2013, 4(7):1091-1103.
Haskell, Richard C. et al., "Boundary Conditions for the Diffusion Equation in Radiative Transfer," Journal of the Optical Society of America: A, 1994, 11(10):2727-2741.
Huang, Bo et al., "Three-dimensional Super-resolution Imaging by Stochastic Optical Reconstruction Microscopy," Science, 2008, 319(5864):810-813.
Jalili, Nader et al., "A review of atomic force microscopy imaging systems: application to molecular metrology and biological sciences," Mechatronics, 2004, 14(8):907-945.
Kim, Arnold D. et al., "Light propagation in biological tissue," Journal of the Optical Society of America: A, 2003, 20(1):92-98.
Kim, Seung-Jean et al., "An Interior-Point Method for Large-Scale $\ell^1$-Regularized Least Squares," IEEE Journal of Selected Topics in Signal Processing, 2007, 1(4):606-617.
Klose, Alexander D. et al., "Light transport in biological tissue based on the simplified spherical harmonics equations," Journal of Computational Physics, 2006, 220(1):441-470.
Liemert, André et al., "Analytical Green's function of the radiative transfer radiance for the infinite medium," Physical Review E, 2011, 83(3):1-7.
Liu, Feng et al., "Photostimulated near-infrared persistent luminescence as a new optical read-out from $Cr^{3+}$-doped $LiGa_5O_8$," Scientific Reports, 2013, 3(1554):1-9.
Ma, C.M. et al., "AAPM protocol for 40-300 kV x-ray beam dosimetry in radiotherapy and radiobiology," Medical Physics, 2001, 28(6):868-893.
Milstein, Adam B. et al., "Fluorescence Optical Diffusion Tomography," Applied Optics, 2003, 42:3081-3094.
Nie, Shuming et al., "Nanotechnology Applications in Cancer," Annual Review of Biomedical Engineering, 2007, 9:257-288.
Ntziachristos, Vasilis et al., "Experimental three-dimensional fluorescence reconstruction of diffuse media by use of a normalized Born approximation," Optics Letters, 2001, 26(12):893-895.
Ntziachristos, Vasilis et al., "Looking and listening to light: the evolution of whole-body photonic imaging," Nature Biotechnology, 2005, 23(3):313-320.
Panasyuk, George Y. et al., "Superresolution and Corrections to the Diffusion Approximation in Optical Tomography," Applied Physics Letters, 2005, 87(10)1-7.
Perrault, Steven D. et al., "In vivo assembly of nanoparticle components to improve targeted cancer imaging," PNAS, 2010, 107(25)11194-11199.
Pong, Wing-Tat et al., "A review and outlook for an anomaly of scanning tunnelling microscopy (STM): superlattices on graphite," Journal of Physics D: Applied Physics, 2005, 38(21):R329-R355.
Pratx, Guillem et al., "Tomographic molecular imaging of x-ray-excitable nanoparticles," Optics Letters, 2010, 35(20):3345-3347.
Pratx, Guillem et al., "X-Ray Luminescence Computed Tomography via Selective Excitation: A Feasibility Study," IEEE Transactions on Medical Imaging, 2010, 29(12):1992-1999.
Qian, Ximei et al., "In vivo tumor targeting and spectroscopic detection with surface-enhanced Raman nanoparticle tags," Nature Biotechnology, 2008, 26(1):83-90.
Ricci, C. et al., "Cancer tissue engineering—new perspectives in understanding the biology of solid tumours—a critical review," OA Tissue Engineering, 2013, 1(1):1-7.
Rice, B.W. et al., "In vivo imaging of light-emitting probes," Journal of Biomedical Optics, 2001, 6(4):432-440.
Schweiger, M. et al., "The finite element method for the propagation of light in scattering media: Boundary and source conditions," Medical Physics, 1995, 22(11):1779-1792.
Solanki, Aniruddh et al., "Nanotechnology for regenerative medicine: nanomaterials for stem cell imaging," Nanomedicine, 2008, 3(4):567-578.

(56) References Cited

OTHER PUBLICATIONS

Sunderland, Christopher J. et al., "Targeted Nanoparticles for Detecting and Treating Cancer," *Drug Development Research*, 2006, 67(1):70-93.
Timpson, Paul et a, "Imaging molecular dynamics in vivo—from cell biology to animal models," *Journal of Cell Science*, 2011, 124(17):2877-2890.
Vila-Comamala, Joan et al., "Zone-doubled Fresnel zone plates for high-resolution hard X-ray full-field transmission microscopy," *Journal of Synchrotron Radiation*, 2012, 19(5):705-709.
Wang, Ge et al., "In vivo mouse studies with bioluminescence tomography," *Optics Express*, 2006, 14(17):7801-7809.
Wang, Ge et al., "Uniqueness theorems in bioluminescence tomography," *Medical Physics*, 2004, 31(8):2289-2299.
Wang, Lihong V. "Multiscale photoacoustic microscopy and computed tomography," *Nature Photonics*, 2009, 3(9):503-509.
Weissleder, Ralph et al., "Shedding Light onto Live Molecular Targets," *Nature Medicine*, 2003, 9(1):123-128.
Withers, Philip J. "X-ray nanotomography," *Materials Today*, 2007, 10(12):26-34.
Wongsrichanalai, Chansuda et al., "A Review of Malaria Diagnostic Tools: Microscopy and Rapid Diagnostic Test (RDT)," *American Journal of Tropical Medicine and Hygiene*, 2007, 77(Suppl 6):119-127.
Wu, Syue-Ren et al., "Hard-X-ray Zone Plates: Recent Progress," *Materials*, 2012, 5(10):1752-1773.

\* cited by examiner

FIG. 2C
FIG. 2D
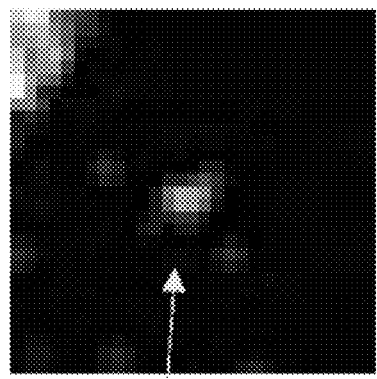
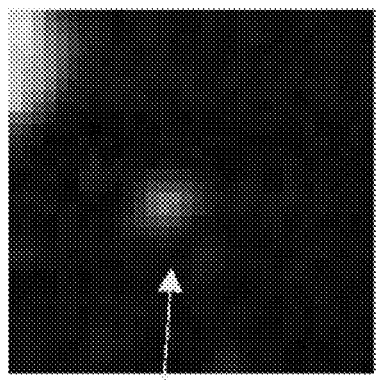
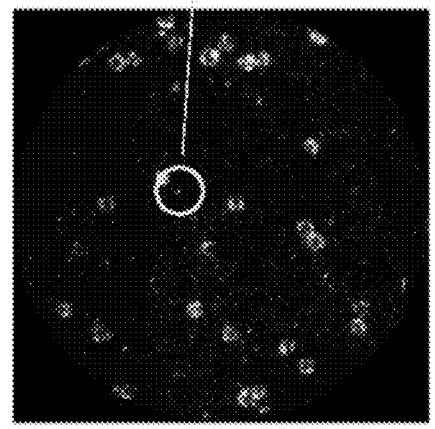
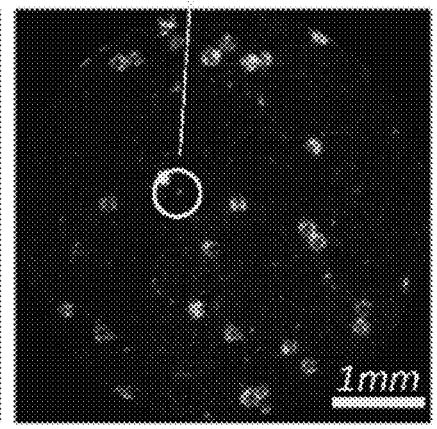
FIG. 2A
FIG. 2B

FIG. 2F
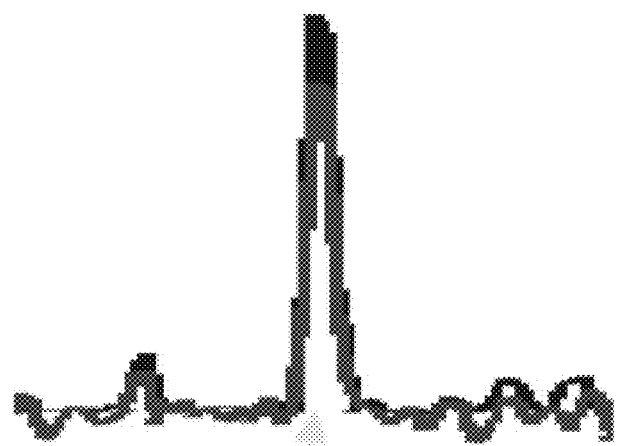
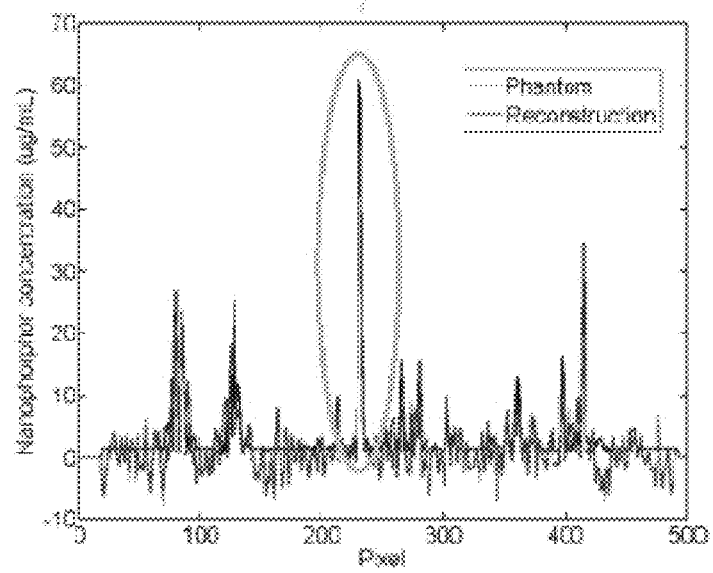
FIG. 2E

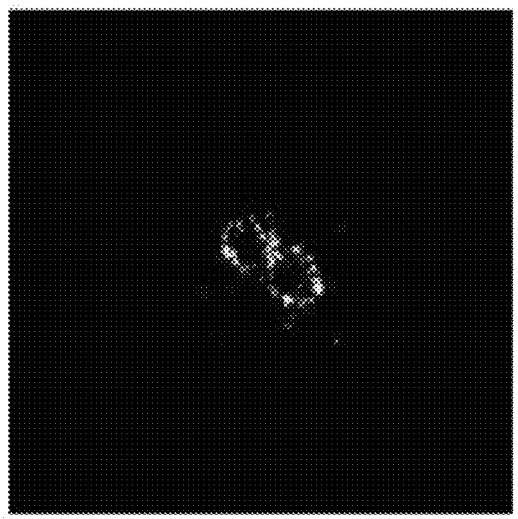
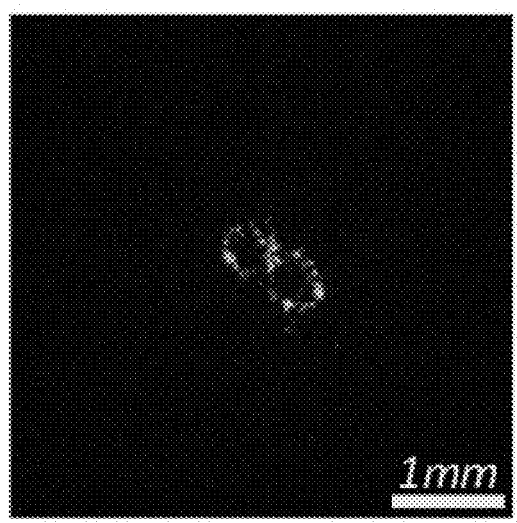
FIG. 2G  FIG. 2H
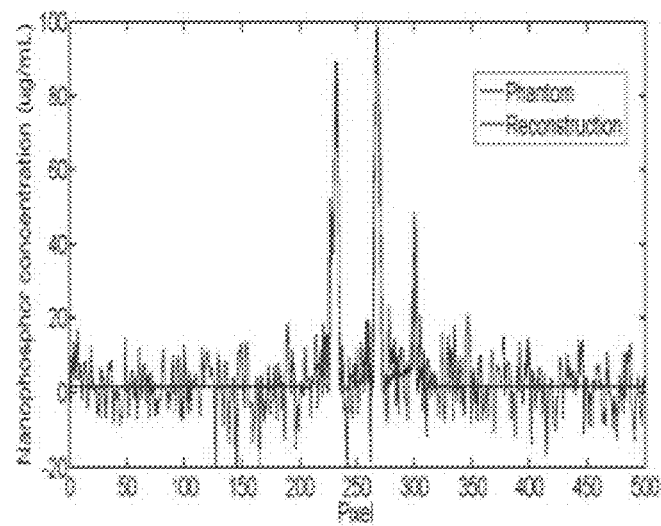
FIG. 2I

STORED LUMINESCENCE COMPUTED TOMOGRAPHY

CROSS-REFERENCE TO A RELATED APPLICATION

The present application claims the benefit of U.S. Provisional Application Ser. No. 61/912,589, filed Dec. 6, 2013 and U.S. Provisional Application Ser. No. 61/916,464, filed Dec. 16, 2013, both of which are incorporated by reference herein in their entirety, including any figures, tables, and drawings.

BACKGROUND OF INVENTION

Systems biology is devoted to comprehensive studies of biological components with interrelated mechanisms across resolution scales over six orders of magnitude, involving molecules, sub-cellular features, cells, organisms, and entire species. Living systems are highly complicated, dynamic, and often unpredictable. To understand and manipulate these systems, quantitative measurements of interacting components and clusters are necessary using systematic and microscopic technologies such as microscopies, genomics, proteomics, bioinformatics, in vivo or in situ imaging, and computational models. Regenerative medicine utilizes principles of biology and engineering to develop and transplant engineered substitute tissues and organs, with various protocols for cell seeding onto porous scaffolds during incubation. These constructs are then expected to restore or regenerate functionality of diseased tissues or organs. Engineered tissue growths are rather sophisticated, and as natural biological counterparts, they usually recapitulate normal developmental processes. Hence, systematic and microscopic technologies are critical for evaluating engineered tissue prior and post implementation.

Microscopy is the principal observational tool and has made important contributions to the understanding of biological systems and engineered tissues. However, imaging depth of optical microscopy has been fundamentally limited to millimeter or sub-millimeter due to multiple scattering of light in a biological sample. Conventional microscopy techniques utilize visible light or electron sources. Optical microscopy can be divided into transmission (i.e., wide-field microscopies for snap-shot of 2D images in terms of light absorption, phase contrast, or dark-field signals) and emission modes (i.e., wide-field fluorescence microscopy, confocal laser scanning microscopy, and two-photon fluorescence microscopy).

These microscopic modalities can be used for in vitro and in vivo studies of cultured cell/tissue samples or small animals. Image resolution of optical microscopy is diffraction limited to about 200 nm with single objective techniques and about 120 nm with confocal techniques. With appropriate sample preparation, stochastic information and innovative interference techniques, about 100 nm resolution may be achievable. Three-dimensional image cubes can be obtained with optical sectioning of about 200 nm lateral resolution and about 500 nm axial resolution.

Ultimately, multiple scattering prevents these techniques from imaging thick samples. Photoacoustic tomography permits scalable resolution at imaging depths up to about 7 cm with a depth-to-resolution ratio about 200. Photoacoustic microscopy aims at millimeter imaging depth, micron-scale resolution and absorption contrast, which could be used to characterize the structure of the scaffold but is generally not as sensitive and specific as fluorescence and bioluminescence imaging.

BRIEF SUMMARY

The subject invention provides novel and advantageous imaging methods and imaging systems, capable of overcoming the limitations of related art imaging methods and systems. Methods and systems of the subject invention can include the use of nanoparticles (for example, nanophosphors) within a sample to be imaged. Stimulation with infrared light, such as near-infrared (NIR) light, and/or optical multiplexing can be used to acquire tomographic data of the sample. In certain embodiments, X-ray engraving can be performed and/or X-ray excitation can be used to provide energy (that can then be stored) to the nanoparticles. If energy is stored in the nanoparticles, it can be released when NIR light is provided.

In an embodiment, an imaging method can include: using an X-ray source to engrave a distribution pattern of nanoparticles within a sample to be imaged; and acquiring tomographic data of the sample. Acquiring tomographic data of the sample can include: stimulating the sample with infrared light from at least one light source to cause the nanoparticles to emit light; and capturing the light emitted by the nanoparticles using at least one camera facing the sample. The nanoparticles can be nanophosphors, though embodiments are not limited thereto.

In another embodiment, an imaging system can include: a stage for a sample to be imaged; an X-ray source configured to engrave a distribution pattern of nanoparticles within a sample to be imaged; at least one infrared light source configured to provide infrared light to stimulate a sample to be imaged; at least one camera for capturing light emitted from a sample to be imaged; and an optically-opaque cover within which the stage, the X-ray source, the at least one infrared light source, and the at least one camera are contained.

BRIEF DESCRIPTION OF THE DRAWINGS

The patent or application file contains at least one drawing executed in color. Copies of this patent or patent application publication with color drawings will be provided by the Patent Office upon request and payment of the necessary fee.

FIG. 2A shows an image of true nanophosphor distribution at 2.5 mm depth.

FIG. 2B shows an image of reconstructed nanophosphor distribution with about 10 μm resolution.

FIG. 2C shows an enlarged view of the circled portion in FIG. 2A.

FIG. 2D shows an enlarged view of the circled portion in FIG. 2B.

FIG. 2E shows a profile comparison along the vertical line at x=160th pixel between true and reconstructed nanophosphor concentrations.

FIG. 2F shows an enlarged view of the circled portion in FIG. 2E.

FIG. 2G shows an image of true nanophosphor distribution at 3.5 mm depth

FIG. 2H shows an image of reconstructed nanophosphor distribution.

FIG. 2I shows a profile comparison along the horizontal center-line between true and reconstructed nanophosphor concentrations.

DETAILED DISCLOSURE

Figure 1:
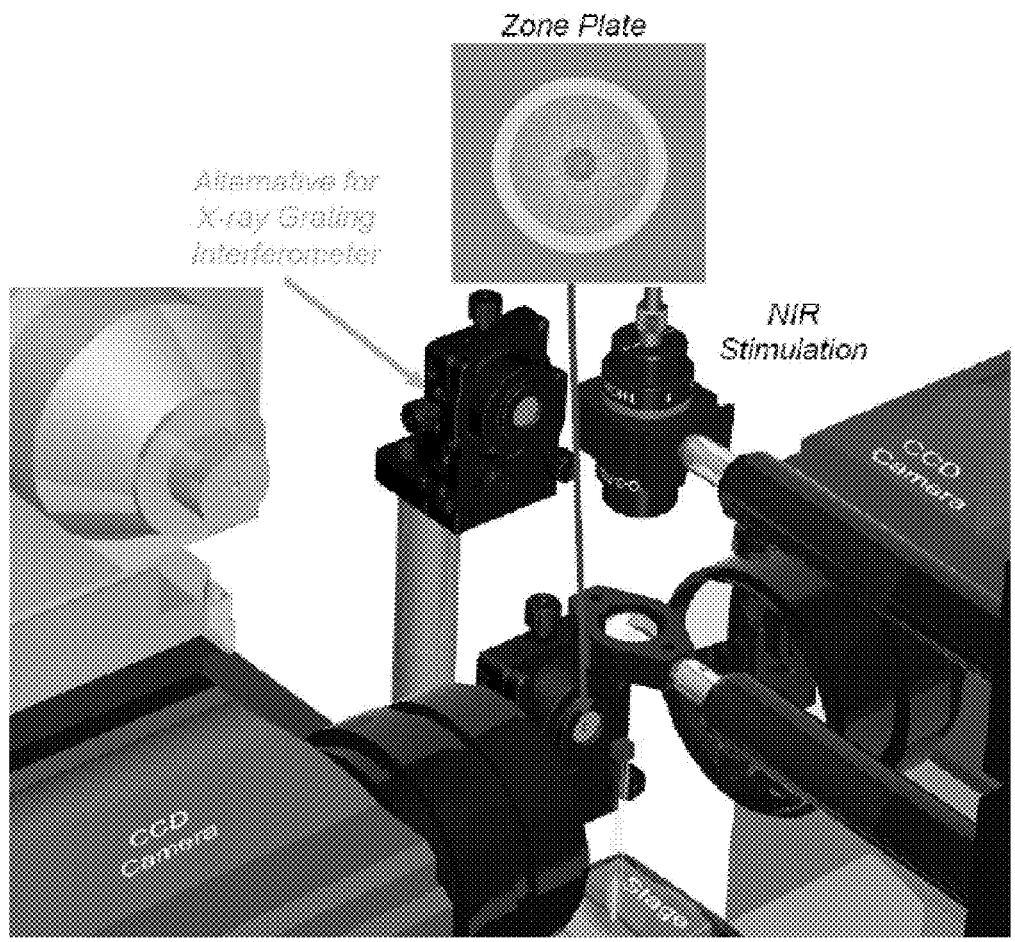
FIG. 1 shows a diagram of a micro-modulated luminescence tomography (MLT) system according to an embodiment of the subject invention.

The subject invention provides novel and advantageous imaging methods and imaging systems, capable of overcoming the limitations of related art imaging methods and systems. Methods and systems of the subject invention can include the use of nanoparticles (for example, nanophosphors) within a sample to be imaged. Stimulation with infrared light, such as near-infrared (NIR) light, and/or optical multiplexing can be used to acquire tomographic data of the sample. In certain embodiments, X-ray engraving can be performed and/or X-ray excitation can be used to provide energy (that can then be stored) to the nanoparticles. If energy is stored in the nanoparticles, it can be released when NIR light is provided.

In certain embodiments, a system can include at least one camera for acquiring imaging data. Such a camera can be, for example, a charge coupled device (CCD) camera such as an electron multiplying charge coupled device (EMCCD) camera, though embodiments are not limited thereto. The system can include an X-ray source, which can be an X-ray tube and/or an X-ray collimator, though embodiments are not limited thereto. The system can further include a stage for a sample to be imaged. The system can also include an optically opaque cover over the system such that the system is shielded from outside light sources. The optically opaque cover can be opaque to all or a portion of the electromagnetic spectrum. For example, the optically opaque cover can be opaque to visible light, infrared light, ultraviolet light, X-ray light, radio waves, or any combination thereof. In certain embodiments, the optically opaque cover can be made of metal (e.g., aluminum) and/or blackened panels.

In an embodiment, a system can include a micro-focus X-ray source, an X-ray zone plate, at least one camera, at least one NIR laser stimulation source, and a stage. The stage can be a rotating stage, and each camera can be a CCD camera (e.g., an EMCCD camera).

In an embodiment, a system can include a high sensitivity camera, a mirror imaging device, an X-ray tube, an X-ray collimator, a laser diode, and a sample stage. The laser diode can be an NIR laser diode, and the camera can be a CCD camera (e.g., an EMCCD camera). The mirror imaging device can include one or more mirrors. In certain embodiments, the mirror imaging device can include two mirrors. The sample can be placed on the stage in a transparent container.

Embodiments of the subject invention have a wide variety of applications, including but not limited to providing high-resolution and location-focused tomographic images, monitoring drug delivery, and assessing cancer therapy.

Molecular and cellular probes have versatile and sophisticated labeling capabilities, and are instrumental for systems biology, tissue engineering, and molecular medicine. Biocompatible nanoparticles can be very advantageous for in situ or in vivo molecular imaging, drug delivery, and therapy. Optical imaging is a primary methodology to sensitively visualize nanoparticles tagged to specific molecules and cells. A typical example of the use of biocompatible nanoparticles is cancer research, which employs nanoparticles to deliver drug, heat, or light to cancer cells. Another example is tissue engineering. With multifunctional nanoparticles, engineered tissue constructs can not only be monitored at cellular and molecular levels but also stimulated and regularized by multiple physical means for optimal functionalities. These nanoparticle ingredients are particularly important for the paradigm shift from 2D to 3D matrices in tissue engineering.

Nanoparticles can be functionalized as imaging probes, similar to fluorescent and bioluminescent proteins. Unlike conventional nanoparticle probes, $LiGa_5O_8:Cr^{3+}$ nanoparticles have been synthesized to facilitate the luminescence energy storage with X-ray pre-excitation and subsequently stimulate luminescence emission by visible/near-infrared (NIR) light. $LiGa_5O_8:Cr^{3+}$ nanoparticles can be synthesized using, for example, a sol-gel method with lithium nitrate, gallium nitrate, and chromium nitrate as precursors, followed by calcination and wet mechanical grinding. These particles can be single-crystalline with a size of, for example, from 50 nm to 100 nm. Upon UV or X-ray irradiation, they emit an intense photoluminescence band peaking at 716 nm, attributing to the spin-forbidden $2E \rightarrow 4A2$ transition of $Cr^{3+}$ dopants. The energy stored in nanoparticles can sustain for, e.g., 10 hours with detectable NIR persistent luminescence.

Embodiments of the subject invention include the use a micro-modulated X-ray for engraving a distribution of nanoparticles (e.g., nanophosphors), which can then have luminescence energy stored for detailed tomographic imaging deeply in tissue samples. This imaging modality can reveal a distribution of nanoparticles, such as $LiGa_5O_8:Cr^{3+}$ nanoparticles, targeting specific molecular and cellular aggregates, pathways, and responses in engineered tissue samples.

Such tissue samples can be, for example, several millimeters in size and a few microns in resolution; thus, embodiments of the subject invention can overcome the imaging depth limitations of other optical microscopic methods. The micro-modulated process can be referred to as a micro-modulated luminescence tomography (MLT) process, and tomographic data can be acquired via, for example, near-infrared (NIR) light stimulation and optical multiplexing. The MLT principle can be also used for luminescence tomography with traditional nanoparticles (e.g., traditional nanophosphors).

FIG. 1 shows a diagram of an MLT system according to an embodiment of the subject invention. Referring to FIG. 1, in an embodiment, an MLT system can include a micro-focus X-ray source, an X-ray zone plate, at least one camera (e.g., two cameras), at least one NIR laser stimulation source (e.g., a plurality of NIR laser stimulation sources), and a rotating stage. Each camera can be, for example, an electron multiplying charge coupled device (EMCCD) camera, though embodiments are not limited thereto. All the components can be integrated on an optical table in, e.g., a light-proof box. In a particular embodiment, the light-proof box can be made of metal (e.g., aluminum) posts and blackened panels. The X-ray source can be mounted on a horizontally-motorized linear stage for focal plane adjustment, and the object to be studied can be placed on a rotational stage on a 3D combination of linear stages for x-y-z adjustment. NIR laser beams can be expanded and controlled to stimulate nanoparticles for luminescence imaging. The EMCCD camera can have a sensitive matrix (e.g., a 512×512 matrix). The pixel size of the camera can be, for example, 16×16 μm$^2$, though embodiments are not limited thereto. In an embodiment, two cameras can be used and can be positioned to face each other with the object (sample) in between for simultaneous data acquisition. A filter (e.g., a metal filter such as an aluminum filter) can be used to block low energy X-rays and have a spectral peak at, e.g., 10 keV-20 keV. The X-rays can be collimated into a narrow-angle cone-beam to irradiate the Fresnel zone plate. The zone plate can be placed within a five axis lens positioner. The zone plate can focus an incoming monochromatic X-ray beam onto a focal spot.

The zone plate can include a plurality of radially symmetric X-ray transparent rings. The width $dr_n$ of a ring can decrease with increment of its radius $r_n$. The focal length $f$ of a zone plate can depend on its diameter D, outermost zone width $dr_n$, and X-ray wavelength $\lambda$: $f = D \, dr_n/\lambda$. Since an incoming beam from an ordinary X-ray tube is polychromatic, the X-rays can be focused along a focal line segment. When an object intersects the X-ray focal line segment, the exposed nanoparticles (e.g., nanophosphors) in the object can be excited by X-rays and store some X-ray energy. Upon NIR light stimulation, the X-ray energy stored in the nanoparticles (e.g., nanophosphors) will be released via luminescence emission, and can be detected by the camera(s). The intensity of luminescence emission reflects the nanoparticle concentration distribution.

The measured light signal on the surface of a sample can be closely related to the optical parameters of the sample. The reduced scattering coefficient $\mu'_s(\lambda)$ [mm$^{-1}$] relies on luminescence emission wavelength $\lambda$ (nm) and can be approximated by an empirical function:

$$\mu'_s(\lambda) = 10 a \cdot \lambda^{-b} \tag{1}$$

where a and b are respectively tissue-type-specific constants. The organ-specific values for a and b can be found in Prahl ("Optical properties spectra," Oregon Medical Laser Clinic, 2001), the contents of which are hereby incorporated by reference. The tissue absorption is associated with local oxy-hemoglobin (HbO$_2$), deoxy-hemoglobin (Hb), and water (W) concentrations, and the absorption coefficient $\mu_a(\lambda)$ [mm$^{-1}$] is well approximated as the weighted sum of the three absorption coefficients $\mu_{aHbO2}(\lambda)$, $\mu_{aHb}(\lambda)$, and $\mu_{aW}(\lambda)$, which are calculated from the corresponding absorbance spectra:

$$\mu_a(\lambda) = S_B[x\mu_{aHb}(\lambda) + (1-x)\mu_{aHbO_2}(\lambda)] + S_W\mu_{aW}(\lambda), \tag{2}$$

where x=Hb$O_2$/(Hb$O_2$+Hb) is the ratio between oxy-hemoglobin and total hemoglobin concentrations, $S_B$ and $S_W$ are scaling factors respectively.

In many embodiments, MLT involves NIR light stimulation to make energy-stored nanoparticles (e.g., nanophosphors) emit luminescence photons. A light propagation model can help describe interactions of light photons with scattering and absorbing media, which is essential for MLT image reconstruction. For biological samples, the diffusion approximation model, a computationally-efficient approximation to the radiative transport equation (RTE), can break down with small sample size, strong absorbers, near sources, and across boundaries. In that case, either RTE itself or an alternative photon transport model can be used to accurately describe the photon propagation in biological tissue.

For the infinite-space medium, the solution can be obtained via the spherical harmonics approximation, $$\Phi(r) = \sum_{i=1}^{\frac{N+1}{2}} A_i \frac{e^{-v_i r}}{4\pi r} \tag{3}$$

where $v_i$ and $A_i$ are defined as follows. From the initial conditions $D_0(\lambda)=0$ and $D_1(\lambda)=1$, and the recursive formula $D_{n+1}(\lambda) = (2n+1)\mu_n D_n(\lambda) + \lambda n^2 D_{n-1}(\lambda)$, a polynomial can be derived:

$$P(\lambda) = D_{N+1}(\lambda) = \sum_{l=0}^{(N-1)/2} a_l \lambda^l,$$

where $\mu_n = \mu_a + (1 - f_n)\mu_s$ and $f_n$ are the n-th order absorption moment and the expansion coefficient of the phase function respectively. In the case of the Henyey-Greenstein phase function, $f_n = g^n$, where g is an anisotropic factor. From the initial conditions $D_0(\lambda)=1$ and $D_1(\lambda)=\mu_a$, the second polynomial can be obtained:

$$Q(\lambda) = D_{N+1}(\lambda) = \sum_{l=0}^{(N+1)/2} b_l \lambda^l.$$

The polynomial equation $Q(\lambda)=0$ gives a total of (N+1)/2 negative real-valued roots $\lambda_i$. These rots define the values $v_i = \sqrt{-\lambda_i}$ and the coefficients $A_i$ $$A_i = \frac{1}{b_{\frac{N+1}{2}}} \frac{P(\lambda_i)}{\prod_{n=1, n \neq i}^{(N+1)/2} (\lambda_i - \lambda_n)}. \tag{4}$$

For optical imaging of biological samples, the tissue boundary must be taken into account when analyzing the photon propagation. A significant amount of photons go across the tissue boundary and can be detected by a highly sensitive CCD camera. In this scenario, the photon propagation process can be well-modeled using a semi-infinite slab. For that purpose, the extrapolated boundary condition can be used, which is simple and has been shown to agree well with the Monte Carlo (MC) simulation and physical measurement. An image source can be used to construct a fluence rate solution such that $\Phi(x, y, z_z)=0$ holds at an extrapolated boundary at a distance $z_b$ above the surface of the sample, where $$z_b = \frac{1+R_{eff}}{1-R_{eff}} \frac{2}{3(\mu_a + (1-g)\mu_s)} \text{ and}$$

$$R_{eff} \approx -1.4399n^{-2} + 0.7099n^{-1} + 0.6681 + 0.0636n$$

The photon fluence at the boundary is the sum of the contributions from the source and its image, $$\Phi(r) = \sum_{i=1}^{\frac{N+1}{2}} A_i \left( \frac{e^{-v_i r_1}}{4\pi r_1} - \frac{e^{-v_i r_2}}{4\pi r_2} \right), r \in \partial\Omega, \quad (5)$$

where $r_1 = \|r_{src} - r\|$, and $r_2 = \|r - r_{img}\|$. Therefore, the NIR light propagation in the biological sample can be simulated using Eq. (5).

The intensity of the NIR luminescence emission from nanophosphors is decaying with time, and is related to nanoparticle concentration $\rho(r)$ [µg/mL], x-ray intensity $X(r)$ [Watts/mm$^2$], stimulating light intensity $L(r)$ [Watts/mm$^2$], and luminescence photon yield $\varepsilon$. The luminescence emission from nanophosphors can be formulated as $$S(r;t) = \eta L(r)\varepsilon X(r)\rho(r)\exp(-L(r)\eta t), \quad (6)$$

where $\eta$ is stimulation efficiency. X-ray beams can be focused by a zone plate, forming a pair of narrow-angle cones with a common vertex point. When a biological sample with a thickness of, e.g., about 5 mm is centralized around the focus region, several micrometer width X-rays can go through the sample. For example, for a zone plate with a diameter of 0.35 mm, an outer zone width of 100 nm, and a zone height (gold) of 1600 nm, the focal length is 258 mm and the maximum width of X-ray beams through a sample is about 3.39 µm. In practice, the intensity distribution of X-rays around the focal region can be measured using an X-ray detector. The narrow X-ray beam can excite the nanoparticles (e.g., nanophosphors) in the sample, and the luminescence emission from the nanoparticles can be measured on the surface of the sample by the camera(s) (e.g., CCD camera(s)). The total intensity of the measured NIR light can be related to the nanoparticle concentration on a narrow X-ray beam path, if it is assumed that all the nanoparticles in the excited region are completely depleted during each luminescence data acquisition step (otherwise, the total measurement is a weighted integral).

Data sets can be obtained with the first generation CT scanning mode using a parallel-beam excitation and different view angles for MLT reconstruction. To the first order approximation, a model to simulate the luminescence emission from nanophosphors can be obtained. From Equations (5) and (6), the intensity of luminescence emission from the nanophosphors on each X-ray path in the sample can be determined. Hence, a system of linear equations can be obtained:

$$\Phi = A \cdot \rho, \quad (7)$$

where $\Phi$ is a vector of measured photon fluence rates, $\rho$ a vector of nanophosphor concentrations, and A the system matrix. In molecular imaging applications, molecular probes can be attached to cells of a preferred type, and accumulated locally to form nanophosphor clusters. For reconstruction of a sparse image, an advanced compressive sensing (CS) method can produce excellent image quality from far fewer measurements than what is required by the Nyquist sampling theorem. The $l_0$ norm regularization can ensure the sparsest image reconstruction. The equivalence between the $l_1$ and $l_0$ minimization procedures was previously established under the assumption of the restricted isometry property (RIP). Hence, the $l_1$ norm is a valid sparsity measure of a signal, and is a convex function for efficient optimization. The reweighted $l_1$ minimization outperforms the $l_1$ minimization for accurate image reconstruction in the case of even fewer measurements. This algorithm can include solving a sequence of weighted $l_1$-minimization problems. The few-view reweighted sparsity hunting (FRESH) scheme can be used for MLT reconstruction.

In many embodiments, the nanoparticles can be nanophosphors. Nanophosphors emit near-infrared (NIR) luminescence light upon X-ray excitation. As optical probes, nanophosphors potentially allow sensitive and specific high-resolution imaging in vivo. X-ray luminescence computed tomography (XLCT) can be used for preclinical imaging; XLCT combines X-ray and optical imaging to improve image resolution relative to purely optical imaging modalities such as fluorescence tomography and bioluminescence tomography. XLCT utilizes X-ray luminescent nanophosphors (NPs) as imaging probes. NPs can be excited with a pencil, fan, or cone beam of X-rays, and the NPs luminescence can be readily generated and efficiently collected using a sensitive light detection system. XLCT is an analog to fluorescence diffuse optical tomography (FDOT), but the former has an advantage over the latter in terms of penetration depth and photo-stability. XLCT can image the cross-sectional distribution of nanophosphors using pencil beam excitation, the first generation computed tomography (CT) mode. However, this type of luminescent light signals comes from all excited NPs and is highly diffusive, limiting the accuracy of image reconstruction.

Nanophosphors (e.g., MgGa2O4:Cr3+) can be capable of restraining luminescence emission for tens of hours or even longer after one-time X-ray excitation. The stored energy is released upon NIR light stimulation at subsequent time points leading to effectively controlled luminescence emission, for example in the range of 650 nm to 770 nm. The mechanism for the stored luminescence in such NPs lies in the modified energy diagram of the doped semiconductor MgGa2O4:Cr3+ of nearly 44% cationic site inversion due to nominal Mg deficiency. The dopant Cr3+ ions occupy octahedral sites, which are associated with the stored luminescence emission spectrum around 707 nm (corresponding to the dopant associated 2E(2G)→4A2(4F) transition). The advent of such NPs opens a door to significant flexibility and performance gain for molecular and cellular imaging.

Embodiments of the subject invention include methods and devices for stored luminescence computed tomography (SLCT). SLCT is an analog to XLCT, but the former outperforms the latter because stored luminescence can be read out in much more flexible ways than the instantaneous emitted luminescence on which XLCT relies. The freedom for selective data acquisition implies a major improvement on image resolution, holding a great promise for sensitive and specific small animal imaging in general.

Nanoparticles (e.g., MgGa2O4:Cr3+ nanoparticles) can be functionalized to target specific cells and then introduced into an object (sample), for example a living mouse. X-rays from an X-ray tube can be collimated into a narrow beam such as a pencil or fan beam for excitation of regions of interest (ROI) in the sample (e.g., mouse). Part of the X-ray energy can then be deposited in the nanoparticles (e.g., nanophosphors such as MgGa2O4:Cr3+). When stimulated by NIR laser light in various patterns, the pre-excited nanoparticles can emit luminescence photons, for example in the range 650 nm to 770 nm. The retrospectively stimulated luminescence emission data can be collected on the surface of the sample (e.g., mouse) for tomographic image reconstruction.

SLCT imaging includes localizing and quantifying a distribution of energy-storing nanophosphors such as MgGa2O4:Cr3+ nanoparticles in a 3D object, e.g., a mouse. Because the measurement of NIR light signals can be spatially and temporally resolved by stimulating energy-storing nanophosphors at any location on the surface of the object and any time instant as long as the energy remains stored in the nanoparticles, the resultant dataset can carry more tomographic information than the counterpart in a corresponding XLCT experiment. Generally speaking, many problems of optical tomography are under-determined with possible false solutions due to the inherent non-uniqueness and data noise. This issue can be effectively overcome with informative combinations of well-defined X-ray beam shapes and NIR stimulation patterns, such as is done in embodiments of the subject invention.

Two powerful imaging features are unique to SLCT, and are not currently possible with other optical imaging modalities such as XLCT. First, a field of view (FOV) for a SLCT study can be clearly defined with X-rays. This means not only a direct energy distribution from a single X-ray beam but also a synthetic energy distribution from multiple X-ray beams. The latter scheme is an analog to tomotherapy for radiation oncology. Second, an energy distribution carried by energy-storing nanoparticles can be optically read out in a multiplexing fashion. NIR light patterns can be projected externally anywhere around the FOV in a time sequence, which is more effective than measuring all luminescent signals simultaneously from the distribution as a whole. The NIR stimulation patterns can be coded in different frequencies as well. The NIR light penetration depth can depend on its wavelength and intensity. For example, SLCT imaging can be performed in an onion peeling fashion. In other words, external shells can be initially stimulated and reconstructed, depleting X-ray energies in these shells. Then, the subsequent signals must come from internal shells. With such an onion peeling strategy, the FOV can be shrunk in step-by-step fashion for more accurate and more reliable image reconstruction, which is not possible with XLCT, fluorescence tomography, or bioluminescence tomography.

Incident X-rays can be easily collimated into a narrow beam to excite energy-storing nanoparticles (e.g., nanophosphors such as MgGa2O4:Cr3+) in a sample (e.g., a living mouse). The X-ray intensity distribution X(r) in the sample can be described by the Lambert-Beer law:

$$X(r) = X_0 \exp\left(-\int_0^{|r-r_0|} \mu\left(r_0 + t \cdot \frac{r-r_0}{|r-r_0|}\right) dt\right), \quad (8)$$

where r0 is a source position, X0 the incident X-ray intensity, and m the linear attenuation coefficient [mm-1] which can be computed with X-ray CT. Energy stored in the nanoparticles can be determined by local X-ray flux intensities. Therefore, a stored X-ray energy density distribution can be computed inside the sample according to Equation (8). A more desirable X-ray energy distribution can be synthesized using a tomotherapy approach, and an established radiation therapeutic planning technique can be directly applied to deposit a pre-specified X-ray energy distribution such as targeting an ROI.

NIR light can be moderately absorbed and strongly scattered in biological tissues. When a laser beam stimulates the nanoparticles, the luminescence energy stored in the nanoparticles can be released and decreased with time. The time-resolved diffusion approximation (DA) model describes this scenario:

$$\frac{\partial \Phi(r,t)}{\partial t} - \nabla \cdot [D(r) \nabla \Phi(r,t)] + \mu_a(r) \Phi(r,t) = S(r,t), r \in \Omega \quad (9)$$

where r is a position vector, $\Phi(r,t)$ an NIR fluence rate, $S(r,t)$ an NIR source, $\mu_a$ the absorption coefficient [mm-1], $D=[3(\mu_a+\mu'_s)]^{-1}$, $\mu'_s$ the reduced scattering coefficient [mm-1], and $\Omega \subset R^3$ the imaging region of the object. If no NIR photon at the wavelength of nanophosphor emission travels across the boundary $\partial\Omega$ into the tissue domain $\Omega$, the DA is constrained by the Robin boundary condition $$\Phi(r,t)+2\alpha D(r)(v \cdot \nabla \Phi(r,t))=0, r \in \Omega, \quad (10)$$

where n is the outward unit normal vector on ¶W, and a the boundary mismatch factor. The boundary mismatch factor between the tissue of a refractive index n and the air can be approximated by $\alpha=(1+\gamma)/(1-\gamma)$ with $\gamma=-1.4399n^{-2}+0.7099n^{-1}+0.6681+0.0636n$ Thus, the measurable exiting photon flux on the surface of the sample can be expressed as $$m(r,t)=-D(r(v \cdot \nabla \Phi(r,t)), r \in \partial\Omega. \quad (11)$$

The intensity of the NIR luminescence emission depends on the concentration of the nanoparticles $\rho(r)$, the x-ray intensity $X(r)$, the stimulation light intensity $L(r)$, and the luminescence photon yield $\varepsilon$. The source term is written as $$S(r,t)=\eta L(r) \varepsilon X(r) \rho(r) \exp(-L(r)\eta t), \quad (12)$$

where the stimulation light intensity distribution can be calculated via Monte Carlo simulation or diffusion approximation model, and $\eta$ is the stimulation efficiency. The solution of Equations (9) and (10) can be expressed with the Green function:

$$\Phi(r,t) = \int\int_\Omega G(r,r',t) S(r,t) dr'. \quad (13)$$

In this context, the image reconstruction is performed in an "onion-peeling" fashion. Peripheral shells can be first stimulated and reconstructed, effectively depleting X-ray energies in these shells. Then, the subsequent signals can mainly come from more and more interior shells. With this time-resolving progressive data acquisition strategy, image reconstruction can be more accurate and more reliable than existing optical molecular tomography techniques. In this way, several exposure times can be used to finish the whole data acquisition process. In the first step with an exposure time T1, the emission can come mainly from nanoparticles immediately below the surface boundary of the sample (e.g., mouse), and the intensity of emission from deeper regions can be very weak due to rather low stimulation power for these regions. The photon fluence rate within T1 exposure time can be modeled by $$\int_0^{T_1} \Phi(r, t)\,dt = \qquad (14)$$

$$\int\int_\Omega \int \left( \int_0^{T_1} G(r, r', t)\exp(-L(r')\eta t)dt \right) \eta L(r')\varepsilon X(r')\rho(r')dr'$$

Continuing NIR light stimulation more deeply inside the sample, the intensity of luminescence signals from deeper locations can increase over time. For example, with the second exposure of the camera (e.g., CCD camera), the measured photon fluence rate can mainly come from a little further depth, while the nanoparticles near the boundary surface have nearly released all stored energy. At this time, Equation (15) can be solved to reconstruct the nanoparticle concentration within a deeper shell from the measured fluence dataset at the second exposure time:

$$\int_{T_1}^{T_2} \Phi(r, t)\,dt = \qquad (15)$$

$$\int\int_\Omega \int \left( \int_{T_1}^{T_2} G(r, r', t)\exp(-L(r')\eta t)dt \right) \eta L(r') \in X(r')\rho(r')dr'$$

The procedure can be repeated until all stored luminescence energy is depleted. Finally, all reconstructed components can be integrated to form an overall nanoparticle distribution image.

Equations (14) and (15) can be discretized into a linear equation system with respect to the nanophosphor concentration. Based on the image characteristics encountered in the biomedical imaging applications, targeting nanoparticles are often attached to cells of a preferred type and accumulated locally, forming a sparse and/or smooth distribution of nanoparticles. Using a compressive sensing (CS) technique, a nanophosphor concentration distribution can be reconstructed. An interior-point method can be applied to solve a large-scale l1-regularized optimization problem, aided by the preconditioned conjugate gradient direction. An important property of the $l_1$-regularized optimization is that a bound can be computed on the sub-optimality of $\rho$ to accelerate the convergence of iteration.

Figure 3A:
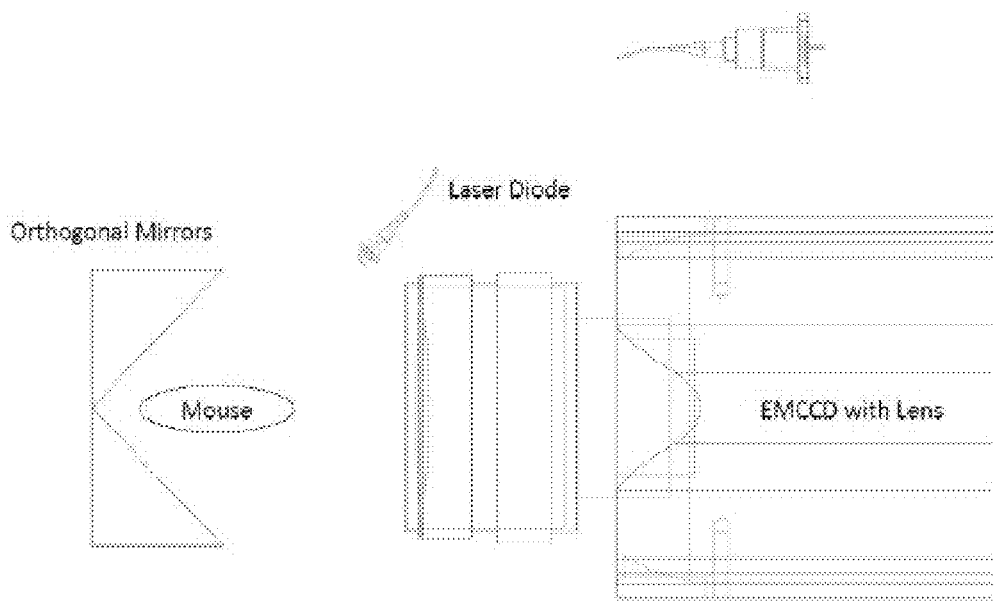
FIG. 3A shows a schematic of a stored luminescence computed tomography (SLCT) system according to an embodiment of the subject invention.
Figure 3B:
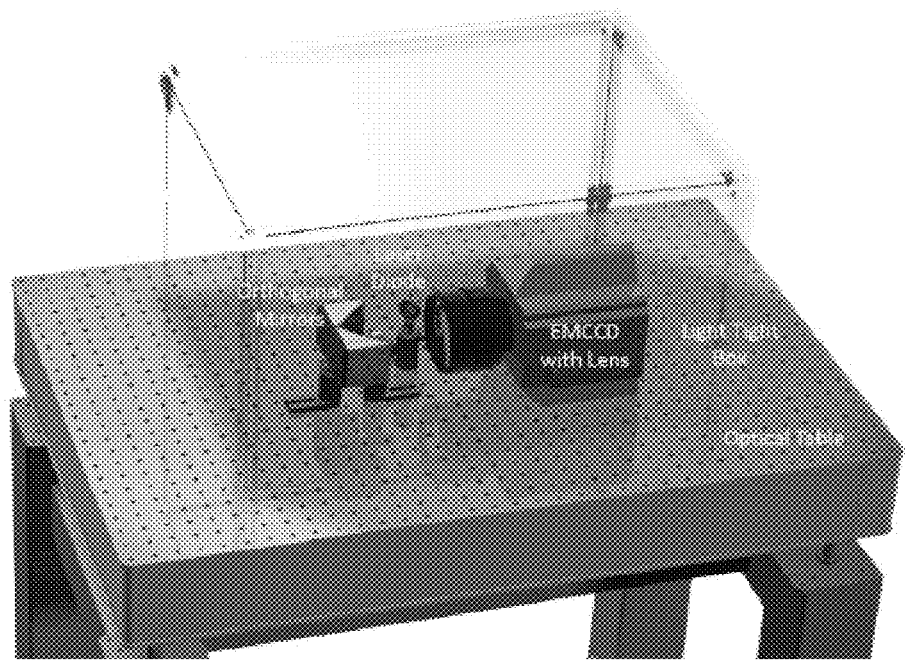
FIG. 3B shows a diagram of an SLCT system according to an embodiment of the subject invention.

FIG. 3A shows a schematic of an SLCT system according to an embodiment of the subject invention, and FIG. 3B shows a diagram of the SLCT system. Referring to FIGS. 3A and 3B, the simulated imaging system can include a high sensitivity camera (e.g., an EMCCD camera), a mirror imaging device, an X-ray tube, an X-ray collimator, a laser diode, and a sample stage. The camera can have, e.g., a 512×512 resolution, a 16 μm×16 μm pixel size, and >90% QE. The camera can face two mirrors of the mirror imaging device, and the sample stage can be mounted on a motorized linear stage for focal plane adjustment. The two-mirror position can be adjusted by another linear stage. A sample (e.g., a mouse with a lie prostrate position) can be contained in a transparent box positioned between the two mirrors, which are easy to implement for in vivo experiments. The two-mirror configuration can be used to expand the field of view of the camera and acquire two views of the sample simultaneously. The entire imaging system can be housed within an optically opaque box.

The Green function can also be expressed as follows:

$$\Omega(r,t) = \int_0^t \int_\Omega G(r,r',t-t')S(r',t')dr'dt', r \in \partial\Omega. \qquad (16)$$

The Green function can be computed using a finite element method. In an imaging mode according to an embodiment of the subject invention, peripheral shells can first be stimulated to effectively deplete X-ray energies in these shells. As time goes by, NIR light would stimulate NPs more deeply inside the object, and most luminescence photons collected on the surface would be more due to NP emissions from more interior locations. The data acquisition process can be conducted during multiple time windows defined by exposure times $t_1, t_2, \ldots, t_n$ to resolve NPs spatially. As a result, a time series of fluence rate data on the surface of the object can be obtained:

$$\int_0^{t_1} \Phi(r;t)dt, \int_{t_1}^{t_2}\Phi(r;t)dt, \ldots, \int_{t_{n-1}}^{t_n}\Phi(r;t)dt, r\in\partial\Omega. \qquad (17)$$

From Equation (16), a time-dependent linear equation system can be established with respect to the NP concentration to describe the relation between the NP concentration distribution $\rho(r)$ and measurable photon fluence rates, $$\Phi[\int_0^{t_1}\Phi(r;t)dt, \int_{t_1}^{t_2}\Phi(r;t)dt, \ldots, \int_{t_{n-1}}^{t_n}\Phi(r;t)dt], \qquad (18)$$

on the surface of an object:

$$A \cdot \rho = \Phi; \qquad (19)$$

where A is a system matrix, which is a discretized Green function in Equation (16). Based on the image characteristics encountered in the biomedical imaging applications, NPs as optical probes can be attached to cells of a preferred type and accumulated locally, forming a sparse distribution of NPs. Compressive sensing (CS) techniques can achieve high-quality image reconstruction from fewer measurements than that required by the Nyquist sampling theorem. Using the CS approach, an NP distribution can be reconstructed. This inverse solution can be transformed to an unconstraint optimization using an interior-point method. The preconditioned conjugate gradients (PCG) algorithm can be used to compute the search direction for the truncated Newton iteration. An important property of the CS-inspired $l_1$-regularization is that a bound on the suboptimality of the NP concentration can be computed by constructing a dual feasible point, accelerating the convergence rate of the iterative procedure.

Figure 6:
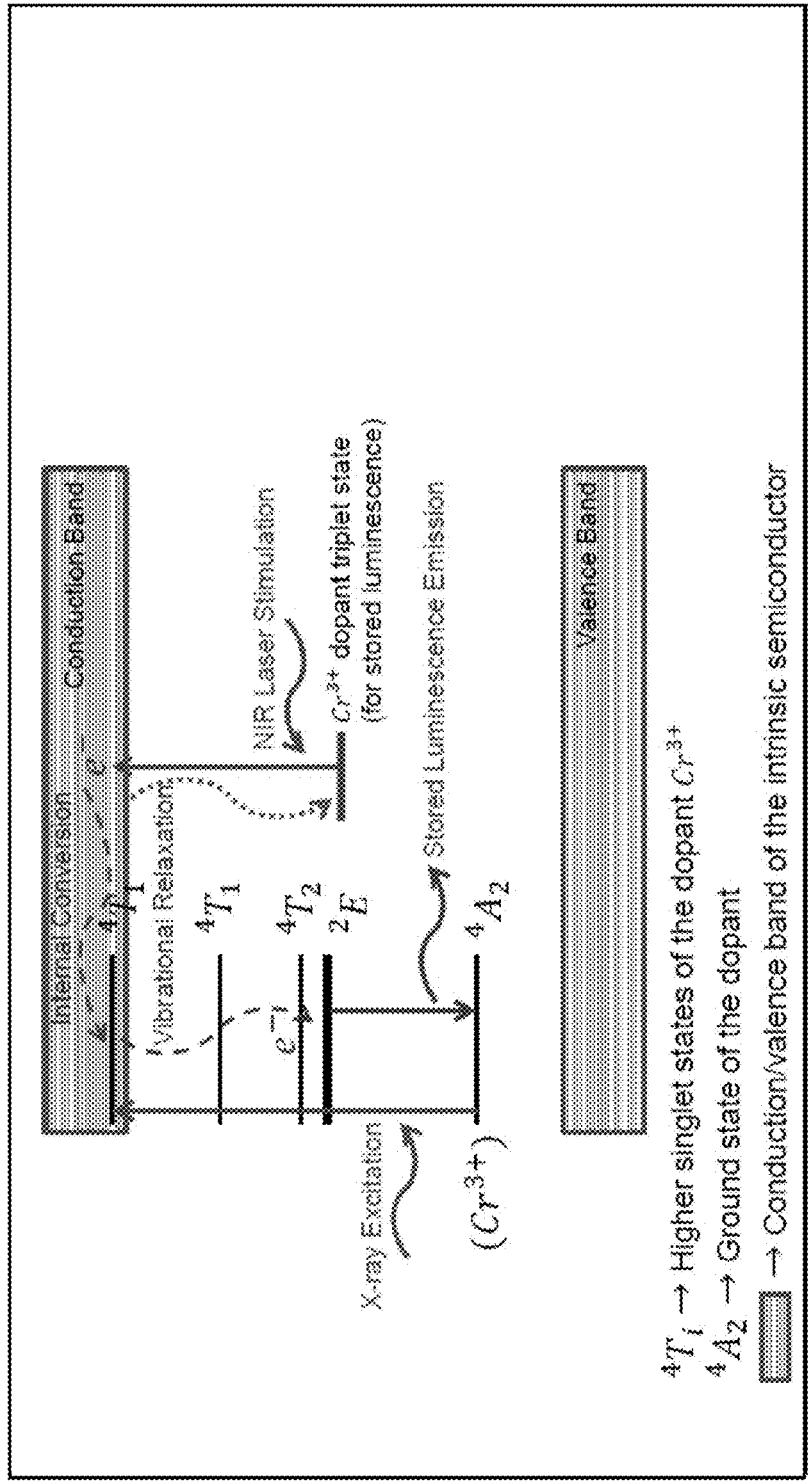
FIG. 6 shows an energy diagram of a doped semiconductor.

The energy diagram of the doped semiconductor for stored NP luminescence is shown in FIG. 6.

In an embodiment, dual-cone geometry can be used for micro-focused X-ray excitation of a three-dimensional (3-D) distribution of nanoparticles (e.g., nanophosphors) in a biological sample or a small animal. Using a polycapillary lens, divergent X-rays can be redirected onto a focal spot of a few micrometers in size, maximizing the intensity of X-ray energy at the vertex point of a double-cone beam. Measurement of the photon fluence on the object surface mainly reflects the optical emission at the vertex point, which is determined by the concentration distribution of nanoparticles (e.g., nanophosphors). This imaging mode can resolve nanoparticles targeting to specific cellular features of a few microns in size and overcome the imaging depth limit of existing microscopic imaging methods.

In an embodiment, an imaging system can include a micro-focus X-ray source, a polycapillary lens, and a camera (e.g., an EMCCD camera). All the components can be integrated on an optical table in a light-proof box. The light-proof box can be made of, e.g., metal (such as aluminum) posts and blackened panels. The X-ray source can be mounted on a horizontally motorized linear stage for adjustment of a focal plane. The EMCCD camera can be mounted to acquire optical signals on the surface of the object. The polycapillary lens bends an incoming X-ray beam onto a focal spot to form double-X-ray cone beams with the focal spot as the common vertex. When the focused X-ray cone irradiates a sample (e.g., biological sample or a small animal) that contains a distribution of nanoparticles (e.g., nanophosphors), the nanoparticles are excited to emit NIR or visible light. The resultant optical signals can be captured by the camera. The (sample) object can be fixed on a stage attached to a combination of linear stages to perform point-by-point scanning in 3-D. From the measured optical data on the object surface, the image reconstruction can be performed to localize and quantify the distribution of nanoparticles (e.g., nanophosphors).

Figure 9:
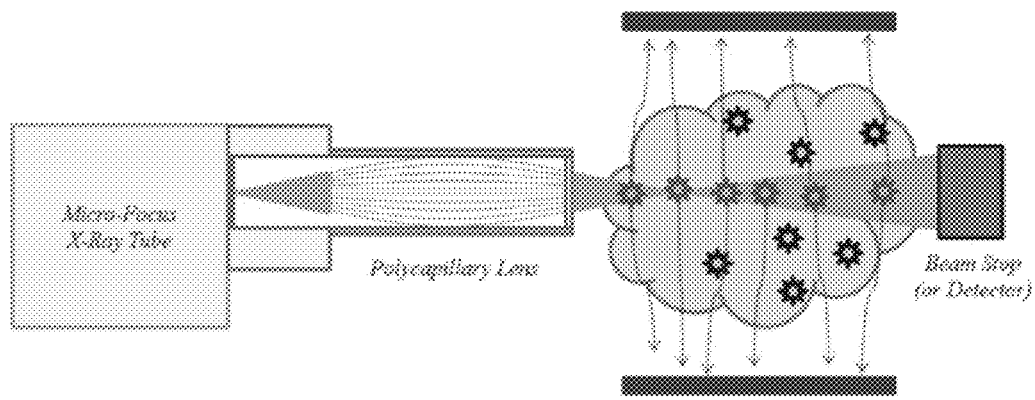
FIG. 9 shows a diagram of an imaging system according to an embodiment of the subject invention.

A lens element is required to focus an X-ray beam and form the requisite double-cone geometry. A Fresnel zone plate is one such focusing element, but it is of low efficiency and restricted to work with nearly monochromatic beams such as that produced by a synchrotron source. Many of the readily available sources generate X-rays by accelerating electrons into high-z metal targets. X-rays are produced which have a broad spectrum due to bremsstrahlung and characteristic emission. To use these X-rays efficiently, an achromatic lens element, such as the polycapillary optics shown in FIG. 9, is preferred to form double cones of X-rays for excitation of nanoparticles (e.g., nanophosphors).

In an embodiment, a polycapillary lens can include a large number of hollow glass fibers bound in a lenticular shape. Although not a true imaging optic, as the output spot size is independent of the source size, it does capture photons from an X-ray source within a fixed solid angle and send them to a small focal spot. Thus, this arrangement defines a vertex in focus extended into two cones in opposite directions along a principal imaging axis. Several design options are possible with the main trade-offs among beam energy, working distance, and focal spot size. For example, for a 17.4-keV X-ray source (Mo-kα) a focal distance of 20 mm from the lens yields a 45-μm spot in an object. A dual-cone beam with a half angle of nearly 10 degrees can be achieved at a focal distance of 9 mm with a 25-μm spot size in the object. If necessary, increasing the beam energy can further extend the focal distance, as the critical angle shifts with X-ray energy. Table 1 summarizes the operating options.

The propagation of light through biological tissues is a complex process, which involves both absorption and scattering simultaneously. A light propagation model describes the interaction of photons with scattering and absorbing media and is essential for optical tomographic imaging. The diffusion approximation (DA) works well in weakly absorbing and highly scattering media, but would break down with strong absorbers, near sources, and across boundaries.

TABLE 1

| Options for commercial polycapillary optics. | | | | |
|---|---|---|---|---|
| Focal distance (mm) | 2 | 9 | 20 | 50 |
| Focal spot size (μm) | 8 | 25 | 45 | 100 |
| Intensity gain | 6000 | 2200 | 1200 | 400 |
| ~F#/Half angle | 0.7 | 3 | 6.7 | 16.7 |
| (3-mm exit pupil) | 48.6 deg | 9.6 deg | 4.3 deg | 1.72 deg |
| 17.4 keV source | | | | |

Hence, DA only fits well for large biological samples (thickness>10 mm). Without such limitations, the radiative transfer equation (RTE) is an accurate model for photon propagation and can be solved in Monte Carlo simulation or with a numerical solution at a higher computational cost. Based on a DA or RTE model, photon fluence rates on an object surface can be expressed in terms of a Green function:

$$\Phi(r) = \int_\Omega G(r,r')S(r')dr', r \in \partial\Omega, \quad (20)$$

where $\Omega$ is a region of interest (ROI), r is a positional vector, $\Phi(r)$ is a photon fluence rate at a location r (Watts/mm$^2$), and S(r) is the intensity of an NIR light source (Watts·hnm$^3$) in an object. The intensity of NIR light emitted from nanophosphors is related to the nanophosphor concentration $\rho(r)$ to be reconstructed, the X-ray intensity distribution X(r) in the object, and the NIR light yields $\eta$ of the nanophosphors which can be defined as the quantum yield per unit nanophosphor concentration:

$$S(r) = \eta X(r)\rho(r). \quad (21)$$

For nanophosphor imaging, a polycapillary lens can be placed in front of an X-ray source to focus X-rays to a focal spot, forming double cones with their shared vertex inside the object, as shown in FIG. 9. The focus spot size is the key to define the intrinsic spatial resolution of this nanophosphor imaging scheme. The polycapillary lens mostly puts X-ray energy around the focal point. For biological soft tissues, an X-ray intensity distribution in the double cones can be calculated with inverse distance weighting, $X(r) = I_0 W(r,r_0)/\|r-r_0\|^2$, where $r_0$ is the common vertex of the double cones, $I_0$ is the intensity of the X-ray source, and $W(r,r_0)$ is the corresponding aperture function of the double cones with the vertex $r_0$. The acquired data by the camera (e.g., EMCCD camera) at each exposure time mainly reflects the NIR emission around the focal point. All the NIR photons on the surface S of the object measured by the EMCCD camera can be summed up to give a single reading:

$$\oiint \Phi(r)dr = \eta I_0 \int_\Omega \left[\oiint_s G(r,r')dr\right] W(r' \cdot r_0) \frac{\rho(r')}{\|r'-r_0\|^2} dr'. \quad (22)$$

The left hand side of Equation (22) is the total photon fluence rate at each exposure time, and the right hand side of Equation (22) is the convolution of the nanophosphor concentration distribution and the X-ray intensity distribution.

To perform reconstruction of a nanophosphor distribution, the focal point of the X-ray double cones is scanned over all grid points in an ROI. In this way, a sufficient amount of information for ROI-based image reconstruction can be obtained. Specifically, the measured photon fluence rates yield a system of linear integral equations based on Equation (22) can be solved for image reconstruction. Outperforming the fluorescence/bioluminescence tomography models, the tomographic imaging model Equation (22) is well-posed and allows an accurate and stable image reconstruction.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

An MLT system as shown in FIG. 1 was fabricated. The MLT system included a micro-focus X-ray source, an X-ray zone plate, an electron multiplying charge coupled device (EMCCD) camera, NIR laser stimulation sources, and a rotating stage. All the components were integrated on an optical table in a light-proof box made of aluminum posts and blackened panels. The X-ray source was mounted on a horizontally-motorized linear stage (ILS300LM, Newport) for focal plane adjustment. The object to be studied can placed on a rotational stage (URS75BCC, Newport) on a 3D combination of linear stages (VP-25XA, VP-5ZA, Newport) for x-y-z adjustment. NIR laser beams can be expanded and controlled to stimulate nanoparticles for luminescence imaging. The EMCCD camera (iXon3 897, Andor Technology) has a sensitive 512×512 matrix with pixel size 16×16 µm². The two cameras were positioned to face each other with the sample object in between for simultaneous data acquisition. An aluminum filter was used to block low energy x-rays and had a spectral peak at 10 keV-20 keV. The X-rays can be collimated into a narrow-angle cone-beam to irradiate the Fresnel zone plate. The zone plate was placed within a five axis lens positioner (IP-05A, Newport). The zone plate focuses an incoming monochromatic X-ray beam onto a focal spot.

The zone plate included multiple radially symmetric X-ray transparent rings. The width $dr_n$ of a ring decreased with increment of its radius $r_n$. The focal length $f$ of a zone plate depended on its diameter D, outermost zone width $dr_n$, and x-ray wavelength $\lambda$: $f=D\, dr_n/\lambda$. Since an incoming beam from an ordinary X-ray tube is polychromatic, the X-rays are focused along a focal line segment. When an object intersects the X-ray focal line segment, the exposed nanoparticles in the object can be excited by X-rays and store some X-ray energy. Upon NIR light stimulation, the X-ray energy stored in the nanoparticles will be released via luminescence emission, and can be detected by the CCD camera. The intensity of luminescence emission reflects the nanoparticle concentration distribution.

Example 2

A numerical simulation was run to study a biological sample phantom of 5×5×5 mm³ using the system of Example 1. Biologically relevant optical parameters were assigned to the phantom: absorption coefficient $\mu_a$=0.01 mm$^{-1}$, scattering coefficient $\mu_s$=10 mm$^{-1}$ and anisotropy parameter g=0.9. It was assumed that the phantom included two patterns of nanophosphors at 2.5 mm and 3.5 mm in depth respectively, which were adapted from a STORM image, with 100 µg/ml maximum concentration, as shown in FIGS. 2A and 2G. This phantom is representative for nanophosphor molecular probe accumulation, contrast, and spatial resolution. An X-ray source of 5 µm focal spot was filtered by a 0.4-mm-thick aluminum plate for an energy spectrum of 10 keV-20 keV.

A Fresnel zone plate of 0.35-mm diameter was utilized for X-ray focusing into a narrow beam of 10 µm width. The phantom was steered with step size of 10 µm for 512 translations to generate NIR light for a view angle, and rotated 100 times over a 180° angular range to excite nanophosphors in the phantom. NIR light stimulation steps were then applied to read out the stored luminescence energy. The X-ray excitation, NIR stimulation, and luminescence emission were all simulated according to Equation (5).

All luminescence photons from a narrow X-ray beam were collected to define the associated integral, and a sinogram was formed. The simulated luminescence signals on the surface of the phantom were corrupted by 5% Gaussian noise to mimic a real measurement condition. The proposed MLT reconstruction method was applied to estimate the nanophosphor distribution from the simulated data. The reconstructed results were in excellent agreement with the true phantom.

FIG. 2B shows the reconstructed nanophosphor distribution with resolution of about 10 µm at 2.5 mm depth. FIG. 2H is the counterpart distribution at 3.5 mm depth. FIGS. 2E and 2I compare the reconstructed and true profiles at 2.5 mm and 3.5 mm depths, respectively, confirming the quantification accuracy of the MLT reconstructions.

FIG. 2C shows an enlarged view of the circled portion of FIG. 2A, FIG. 2D shows an enlarged view of the circled portion of FIG. 2B, and FIG. 2F shows an enlarged version of the circled portion of FIG. 2E.

Example 3

An SLCT system as shown in FIGS. 3A and 3B was fabricated. The system included a high sensitivity EMCCD camera, a mirror imaging device, an X-ray tube, an X-ray collimator, a laser diode, and a sample stage. The camera had a 512×512 resolution, a 16 µm×16 µm pixel size, and >90% QE. The camera faced two mirrors of the mirror imaging device, and the sample stage was mounted on a motorized linear stage for focal plane adjustment. The two-mirror position can be adjusted by another linear stage. A sample can be contained in a transparent box positioned between the two mirrors, which are easy to implement for in vivo experiments. The two-mirror configuration can be used to expand the field of view of the camera and acquire two views of the sample simultaneously. The entire imaging system was housed within an optically opaque box.

Example 4

Figure 4C:
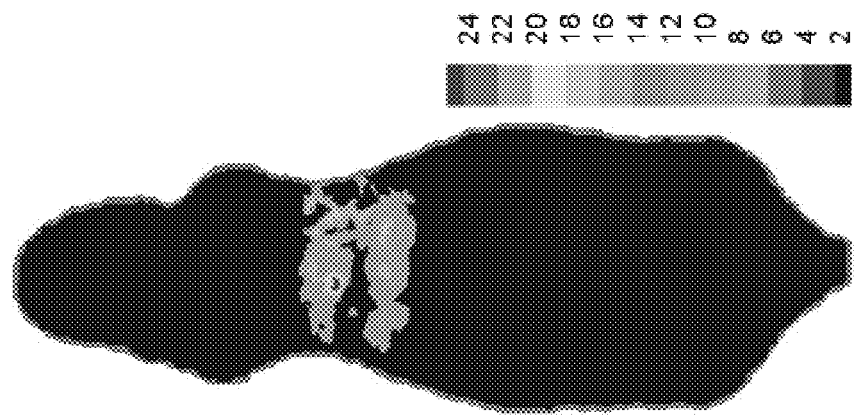
FIG. 4C shows reconstructed nanophosphor concentration distribution in a mouse phantom.
Figure 4B:
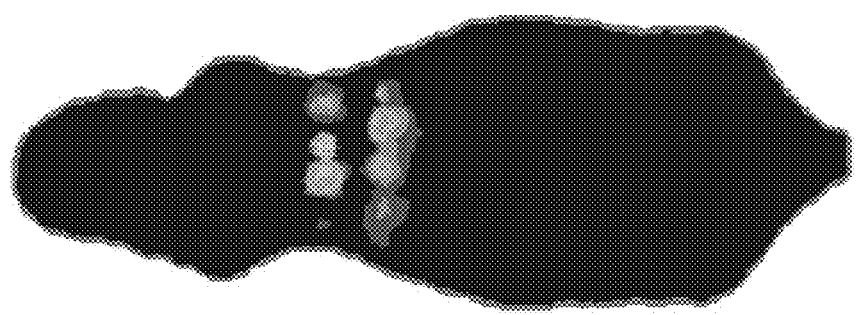
FIG. 4B shows true nanophosphor concentration distribution in a mouse phantom.
Figure 4A:
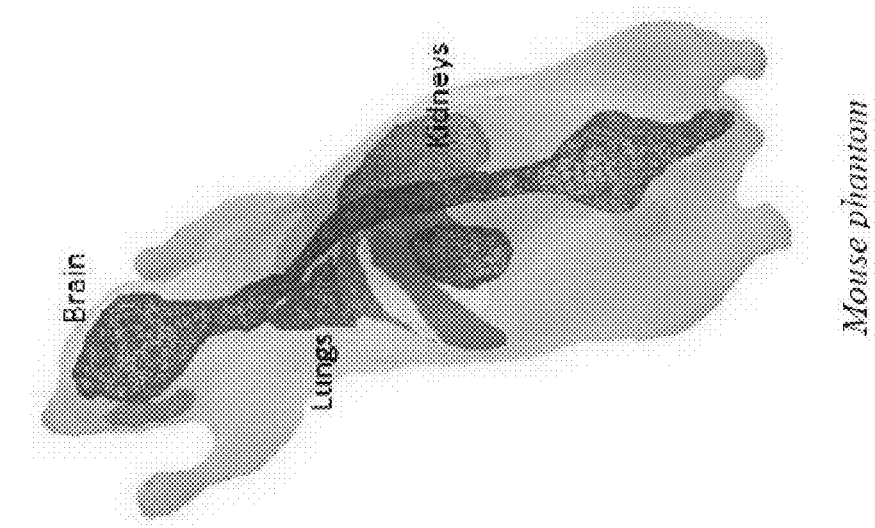
FIG. 4A shows a diagram of a mouse phantom.

A numerical simulation was performed using the SLCT system of Example 3. Representative numerical tests were performed to evaluate the proposed SLCT approach with a digital mouse phantom. As shown in FIG. 4A, the mouse phantom was established from the CT slices of a mouse using Amira (Amira 4.0, Mercury Computer Systems, Inc. Chelmsford, Mass., USA). The phantom was discretized into 306,773 tetrahedral elements with 58,244 nodes. The stored nanophosphor luminescence re-emission peak was chosen as 700 nm, which was based on the emission characteristics of $MgGa_2O_4:Cr^{3+}$. Appropriate optical parameters were assigned to the mouse model accordingly. The reduced scattering coefficient $\mu'_s(\lambda)$ relies on the stored luminescence emission wavelength $\lambda$ (nm) and can be approximated by Equation (1), where a and b are the constants depending on the tissue type. The organ-specific values for a and b can be found in, for example, Alexandrakis et al. ("Tomographic bioluminescence imaging by use of a combined optical-PET (OPET) system: a computer simulation feasibility study," Physics in Medicine and Biology, vol. 50, pp. 4225-4241, September 2005). The tissue absorption can depend on the local oxy-hemoglobin ($HbO_2$), deoxy-hemoglobin (Hb), and water (W) concentrations. The absorption coefficient $\mu_a(\lambda)$ can be approximated as the weighted sum of the three absorption coefficients $\mu_{aHbO_2}(\lambda)$, $\mu_{aHb}(\lambda)$ and $\mu_{aW}(\lambda)$, can be were calculated from Equation (2), where x=$HbO_2$/($HbO_2$+Hb) is the ratio between oxy-hemoglobin and total hemoglobin concentrations, $S_B$ and $S_W$ are scaling factors, respectively. The nanophosphor concentration distribution was set in the mouse lung region from 5

µg/ml to 25 µg/ml. FIG. 4B shows the nanophosphor clusters at the cross section of z=10 mm in the phantom.

XLCT is a synergistic imaging modality defining a permissible source region with X-rays to help reconstruct a distribution of nanophosphors (NPs). These conventional NPs are instantaneously excited by common medical X-rays, and the luminescent data are efficiently collected using a highly sensitive CCD camera. In the first generation CT scanning mode, XCLT uses an X-ray pencil beam excitation, and the emitted light can be measured as a line integral. The classic filtered back projection method can be used to reconstruct an image, with image resolution being decided by the X-ray pencil beam aperture. This scanning mode needs long data acquisition time and is not practical for most preclinical applications. To shorten the scanning time, a cone beam X-ray luminescence computed tomography strategy can be used. In the cone beam stimulation mode, the X-rays illuminate the whole sample to stimulate all the NPs, and a CCD camera acquires luminescent photons for tomographic imaging. This cone beam scanning mode does not sufficiently utilize the primary benefit of XLCT in terms of a reduced permissible source region.

A fan-beam stimulation mode for XLCT can be used, which uses a fan-beam of X-rays to irradiate an object such as a mouse, and the nanoparticles on a cross-section of the mouse emit NIR light. The measured NIR light signal (2D) on the external surface of the object is used to reconstruct a nanoparticle distribution (2D) on the excited cross-section. Theoretically, the dimensionality of measured information matches that of the unknown image. The fan-beam scanning mode is the optimal balance between the pencil beam mode and the cone-beam mode for XLCT in terms of imaging efficiency and image quality, and was focused on in this comparison to show the advantages of SLCT.

An X-ray tube was operated at 50 keV and 30 mA and collimated into a fan beam with a 1 mm thickness. A cross-section was excited at the transverse position of 10 mm of the mouse phantom (see FIG. 4A). The NIR light emission from the excited nanoparticles was recorded on the surface of the phantom by the CCD camera. The collected NIR data were then corrupted by 5% Gaussian noise to simulate practical conditions. A reconstruction method was employed to reconstruct the nanophosphor distribution from the NIR data. The reconstructed image revealed the accumulation of the nanophosphors, and generated a 37% relative error, which was defined as $$\frac{1}{\text{Num}(\rho_k^t > bg)} \sum_{\rho_k^t > bg} \frac{|\rho_k^p - \rho_k^t|}{\max_k(\rho_k^t)}, \qquad (23)$$

where $\rho_k^t$ and $\rho_k^r$ are the true and reconstructed densities on the k-th mesh element respectively, bg was assigned as the background value, and $\text{Num}(\rho_k^t>bg)$ the number of elements in the set $\{k:|\rho_k^t>bg\}$. FIGS. 4B and 4C show a comparison between the true (FIG. 4B) and reconstructed (FIG. 4C) nanophosphor concentration distributions. The reconstructed concentration distribution was determined using XLCT in the fan-beam mode. The unit is µg/ml.

Example 5

The same mouse phantom and parameter settings as in Example 4 were used to evaluate the performance of the proposed SLCT approach. The SLCT experiment was performed in an onion peeling fashion. The phantom was stimulated with laser radiation shell by shell. That is, peripheral regions were first stimulated for "cleaning-up", and the data were collected for recursive image reconstruction. The NIR emission signals were stepwise collected upon the NIR light stimulation, instead of one-time collection for all available luminescence photons as with XLCT. This divide-and-conquer data acquisition procedure ensures that the number of unknowns can be significantly reduced to improve spatial resolution and stability of the image reconstruction. To implement this procedure, two laser beams of 580 nm were used to stimulate the phantom. One laser beam had the same illumination direction as that of the stimulating X-ray beam, while the other laser beam came from the other side of the phantom in the opposite direction of the first laser beam to stimulate the phantom simultaneously.

At the first step, the NIR laser light stimulation mainly excited the peripheral region of the phantom to read-out the nanophosphor stored luminescence near the surface of the phantom. At the same time, a highly sensitive CCD camera acquired the NIR stored luminescence from the nanophosphors. The stimulating laser intensity distribution was calculated by the diffusion approximation model shown in Equation (9) with a known laser source on the surface of the phantom. The laser intensity quickly decayed with the penetration depth. It was assumed that the maximum energy stored in the nanophosphors can be obtained from X-ray pre-excitation, and the laser excitation efficiency of the nanophosphor was set to 60%. Thus, the excitation intensity for a nanophosphor can be calculated. Therefore, the imaging depth for the first shell was determined by excluding the region where the laser intensity was less than the nanophosphor excitation intensity.

Figures 5A, 5B:
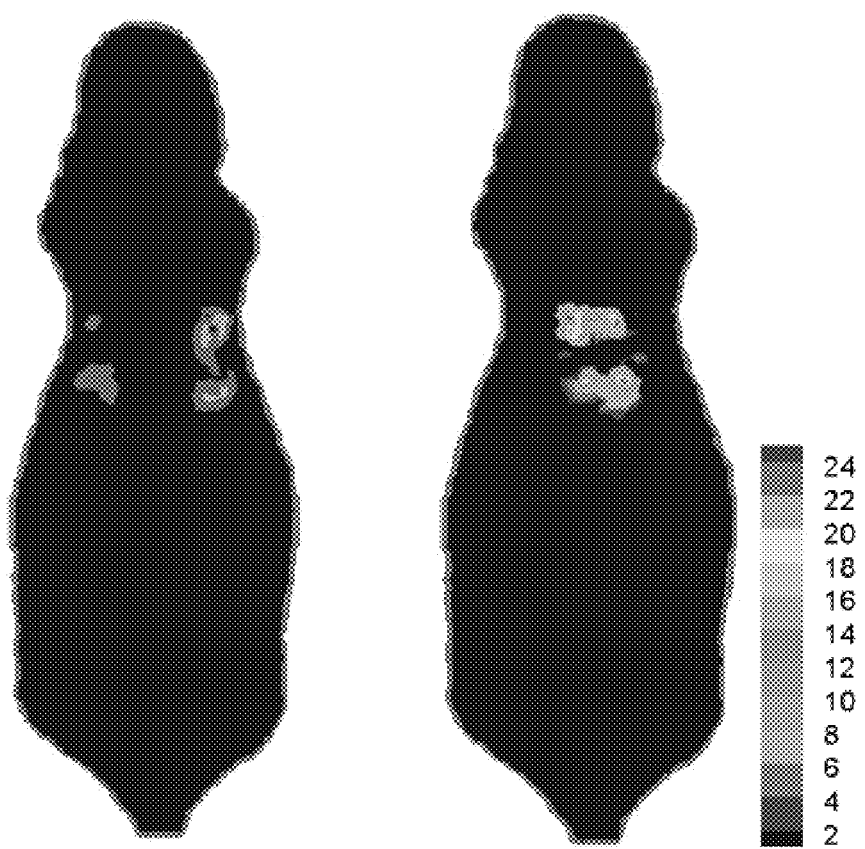
FIG. 5A shows reconstructed nanophosphor concentration distribution in a peripheral region in an object at a first stage of NIR stimulation.
FIG. 5B shows reconstructed nanophosphor concentration distribution in a central region in an object at a second stage of NIR stimulation.

With increasing of the excitation time, the laser penetration depth would increase for imaging of the next shell. The simulated NIR data on the phantom surface were also corrupted by 5% Gaussian noise. A reconstruction method was step-wise/shell-wise employed to reconstruct the nanophosphor distribution from the NIR data. The algorithm gave an excellent performance in terms of convergence and stability. The reconstructed images were in a close agreement with the true values, as shown in FIGS. 5A and 5B, and the averaged relative error of the reconstructed nanoparticle distribution was less than 22%. FIGS. 5A and 5B show the reconstructed nanophosphor concentration distribution in the peripheral region in the object at the first stage of NIR stimulation (FIG. 5A) and the reconstructed nanophosphor concentration distribution in the central region in the object at the second stage of NIR stimulation (FIG. 5B). The true nanophosphor concentration distribution is shown in FIG. 4C. The unit is µg/ml.

Referring to FIGS. 4B, 4C, 5A, and 5B, SLCT is more accurate and more stable than XLCT. This is also shown in Table 2. SLCT performance can possibly be further improved with an optimized NIR excitation scheme.

TABLE 2

Performance comparison between SLCT and XLCT.

| Modality | X-ray Stimulation | MIR Excitation | Stability | Accuracy Error |
|---|---|---|---|---|
| SLCT | Fan beam | Applied | Strong | 22% |
| XLCT | Fan beam | No | Week | 37% |

Example 6

An SLCT system was fabricated, similar to the one of Example 3. The system included a high sensitivity EMCCD camera, a mirror device, an x-ray tube, an x-ray collimator, a laser diode, and a sample stage. The EMCCD camera (iXon3 897, Andor Technology) with a 512×512 resolution, 16 μm×16 μm pixel size, and >90% quantum efficiency. An aluminum filter was used to block low-energy X-rays and achieve a spectral peak at 15 keV to 30 keV. The collimator directs X-rays to an appropriate FOV for excitation of an ROI in the object. The camera faces two mirrors of a mirror imaging device to acquire two views of the sample. The sample stage was mounted on a motorized linear stage for adjustment of a focal plane. A sample can be presented in a transparent box positioned in the middle of the two mirrors. The entire imaging system was housed within an optically opaque box. This imaging setup can be easily implemented for in vivo experiments.

Example 7

Figure 7A:
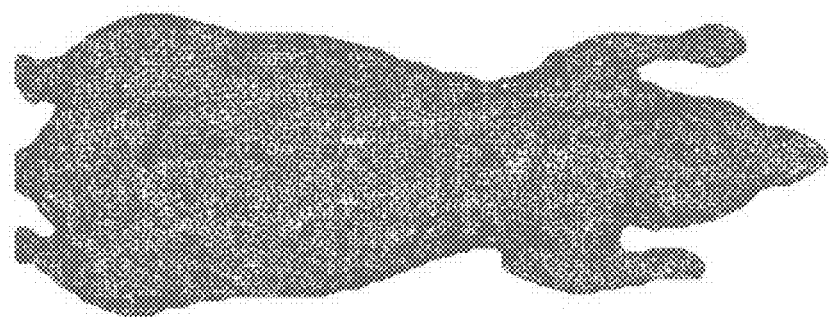
FIG. 7A shows a diagram of a mouse phantom.

A numerical simulation was performed using the SLCT system of Example 6. Representative numerical tests were performed to evaluate the SLCT approach with a digital mouse phantom. As shown in FIG. 7A, the mouse phantom was established from the CT slices of a mouse using Amira (Amira 4.0, Mercury Computer Systems, Inc.). The phantom was discretized into 306,773 tetrahedral elements with 55,457 nodes. The stored NP luminescence emission peak was chosen as 700 nm, which was based on the emission characteristics of $MgGa_2O_4:Cr^{3+}$.

Appropriate optical parameters were assigned to the mouse model accordingly. The reduced scattering coefficient $\mu'_s(\lambda)$ relies on the stored luminescence emission wavelength $\lambda$ (nm) and can be approximated by Equation (1), where a and b are the constants depending on the tissue type. The organ-specific values for a and b can be found in, for example, Alexandrakis et al. ("Tomographic bioluminescence imaging by use of a combined optical-PET (OPET) system: a computer simulation feasibility study," Physics in Medicine and Biology, vol. 50, pp. 4225-4241, September 2005). The tissue absorption can depend on the local oxy-hemoglobin ($HbO_2$), deoxy-hemoglobin (Hb), and water (W) concentrations. The absorption coefficient $\mu_a(\lambda)$ can be approximated as the weighted sum of the three absorption coefficients $\mu_{aHbO_2}(\lambda)$, $\mu_{aHb}(\lambda)$ and $\mu_{aW}(\lambda)$, can be were calculated from Equation (2), where $x=HbO_2/(HbO_2+Hb)$ is the ratio between oxy-hemoglobin and total hemoglobin concentrations, $S_B$ and $S_W$ are scaling factors, respectively.

Figure 8A:
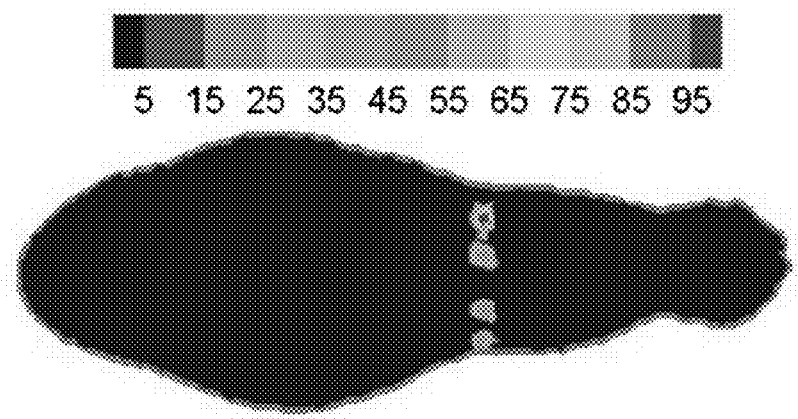
FIG. 8A shows true nanophosphor concentration distribution in a mouse phantom.
Figure 8B:
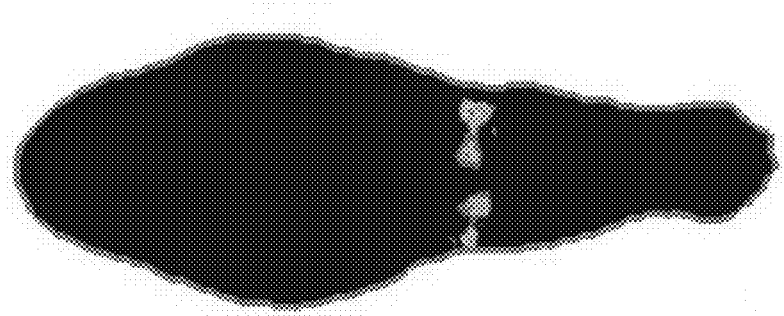
FIG. 8B shows reconstructed nanophosphor concentration distribution in a mouse phantom.

NPs were distributed in the mouse body, where there are four clusters centered on (12.0, 40.0, 14.0), (15.0, 40.0, 14.0), (20.0, 40.0, 14.0), and (23.0, 40.0, 14.0) mm with concentrations of 50, 50, 50, and 100 μg/ml respectively, as shown in FIG. 7A. The NP distribution reflects a twofold difference of concentration in the regions, which was used to test contrast resolution. Two subregions had 0.5 mm separation to test spatial resolution. The X-ray tube was operated at 50 keV and 30 mA to excite the mouse phantom. Three NIR stimulation patterns along the x-axis direction were used to readout the stored luminescence energy in NPs. The NIR luminescence emission from the NPs was recorded on the surface of the phantom by the CCD camera. The collected luminescence emission data were then corrupted by 5% Gaussian noise to simulate practical conditions. A reconstruction method was employed to reconstruct the NP distribution from the simulated NIR dataset. The results show that the reconstructed NP distribution was in excellent agreement with the counterpart in the true phantom, and the average relative error of the reconstructed NP concentration was <25%, which was defined as $$\text{error} = \frac{1}{\text{Num}\{k \mid \rho_k^t > \varepsilon\}} \sum_{\rho_k^t \geq \varepsilon} |\rho_k^r - \rho_k^t| \rho_k^t. \quad (24)$$

where $\text{Num}\{k|\rho_k^t>\varepsilon\}$ represents the total number of elements in the set $\{k|\rho_k^t>\varepsilon\}$, $\varepsilon$ is the noise level, and $\rho_k^t$ and $\rho_k^r$ are the true and reconstructed NPs concentrations, respectively. FIGS. 8A and 8B show a comparison between the true (FIG. 8A) and reconstructed (FIG. 8B) nanophosphor concentration distributions. The unit is μg/ml. Referring to FIGS. 8A and 8B, the accuracy of the SLCT image reconstruction can be seen.

Example 8

Figure 7B:
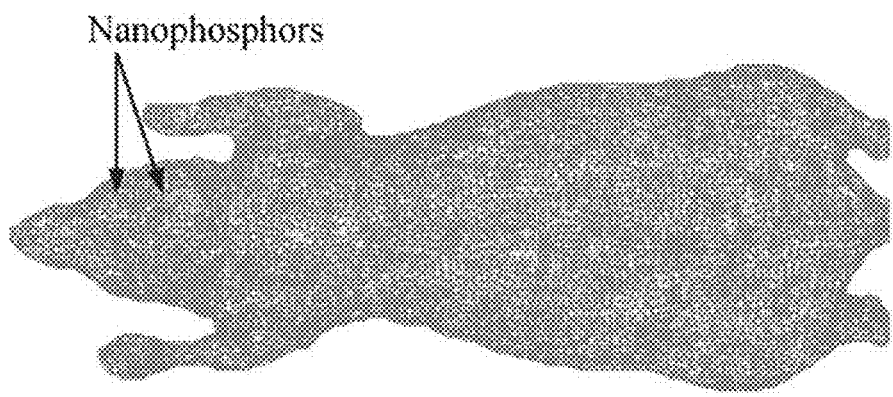
FIG. 7B shows a diagram of a mouse phantom.

A digital mouse model was used to evaluate the reconstruction quality of a nanophosphor distribution for an X-ray micro-modulated luminescence tomography in dual-cone geometry using a system as shown in FIG. 9. The mouse model was discretized into 203,690 tetrahedral elements with 58,244 nodes, as shown in FIG. 7B. The DA model can be employed to describe the NIR light transport process.

$$-\nabla \cdot [D(r)\nabla\Phi(r)] + \mu_a(r)\Phi(r) = S(r), r \in \Omega \quad (25)$$

where r is a positional vector, $\Phi(r)$ a NIR photon fluence rate, $S(r)$ is an NIR source, $\mu_a$ is the absorption coefficient, D is the diffusion coefficient defined by $D=[3(\mu_a+\mu'_s)]^{-1}$, $\mu'_s$ is the reduced scattering coefficient, and $\Omega \subset R^3$ is an object support. If no photon travels across the boundary $\partial\Omega$ into the tissue domain $\Omega$, the DA is constrained by the Robin boundary condition $$\Phi(r) + 2\alpha D(r)[\nu \cdot \nabla \Phi(r)] = 0, r \in \partial\Omega. \quad (26)$$

where $\nu$ is an outward unit normal vector on $\partial\Omega$, and $\alpha$ a boundary mismatch factor. The boundary mismatch factor between the tissue with a refractive index n and air can be approximated by $\alpha=(1+\gamma)/(1-\gamma)$ with $\gamma=-1:4399n^{-2}+0.7099n^{-1}+0.6681+0.0636n$. Thus, the measurable exiting photon flux on the surface of the animal can be expressed as $$m(r) = -D(r)[\nu \cdot \nabla \Phi(r)] r \in \partial\Omega. \quad (27)$$

Equations (25) and (26) can be discretized into a matrix equation linking the nanophosphor distribution $\rho$ and the NIR photon fluence rate $\Phi(r)$ at every node r via finite element analysis:

$$A \cdot \Phi = F \cdot \rho.$$

where the components of the matrix A are $$a_{ij} = \int_\Omega D(r) \nabla \phi_i(r) \cdot \nabla \phi_j(r) dr + \int_\Omega \mu_a(r) \phi_i(r) \phi_j(r) dr + \int_{\partial\Omega} \phi_i(r) \phi_j(r)/2\alpha dr.$$

and the components of the matrix F are $$f_{ij} = \eta I_0 \int_\Omega \frac{W(r, r_0)}{\|r - r_0\|^2} \phi_i(r) \phi_j(r) dr,$$

where $\phi_i$ (i=1, 2, ... ) are the element shape functions. Since the matrix A is positive definite, $$\Phi = (A^{-1}F) \cdot \rho. \quad (28)$$

In the simulation, it was assumed that the polycapillary lens generated double cones of a 19.2-deg angle. Upon X-ray irradiation through nanophosphors $LiGa_5O_8:Cr^{3+}$ (spinel structure), an intense photoluminescence signal was induced, peaking at 716 nm ($Cr^{3+}$R-line emission; spin forbidden $^2E \rightarrow {}^4A_2$ emission transition). The nanophosphors were mainly distributed in the mouse brain, where three subregions, centered on (17.5, 12.5, 12.0), (19.0, 18.0 12.0), and (16.0, 19.0, 12.0) mm, contained nanophosphor concentrations of 1, 4, and 10 µg/ml respectively, as shown in FIG. 7B. The nanophosphor concentrations differed up to ten times in terms of concentrations to test contrast resolution. Two subregions had a 50-µm separation to test the spatial resolution. The intensity of the NIR light on the body surface was simulated according to the DA model. Poisson noise was added to the synthetic data to simulate an experimental environment. In a real in vivo experiment, although the body surface of a mouse is rather arbitrary, a triangular mesh can be constructed to accurately represent the complex geometry. The measured intensity of the NIR light can be mapped via interpolation onto the corresponding triangular elements on the body surface. Based on Equations (22) and (28), $$\sum_{i=1}^{n} \Phi(r_{m_i}) = \left( \sum_{m_i} A^{-1} F \right) \cdot \rho, \quad (29)$$

where $m_i$, (i=1, 2, ..., n) is the index for measured surface nodes. The X-ray double-cone excitation was implemented to cover all the nodes in the ROI={$x^2+y^2 \leq 100$; $-2 \leq z \leq 2$} mm in the animal. Based on Equations (26), (27), and (29), a linear equation system was established with simulated NIR intensity data on the body surface:

$$Q = G \cdot \rho, \quad (30)$$

where Q is the vector of the photon fluence rates from a series of double-cone x-ray excitations, and G is a weighting matrix from Equation (22). The NIR light yield η of the nanophosphors was assumed to be 0.15 $cm^3$/mg for 17.4-keV X-rays. A reconstruction method was applied to estimate the nanophosphor distribution from the simulated dataset.

The results show that the reconstructed nanophosphor concentrations were in excellent agreement with the true counterparts, and the average relative error of the reconstructed nanophosphor concentration was less than 5%, which was defined as error=1/Num{i|$\rho_i^T > \epsilon$}$\Sigma_{\rho_i^T > \epsilon}$|$\rho_i^r - \rho_i^T$|/$\rho_i^T$, where Num{k|$\rho_k^T > \epsilon$} represents the total number of the elements in the set {k|$\rho_k^T > \epsilon$}, ε is a noise level, and $\rho_i^T$ and $\rho_i^r$ are the true and reconstructed concentrations of each nanophosphor cluster, respectively.

Figure 10A:
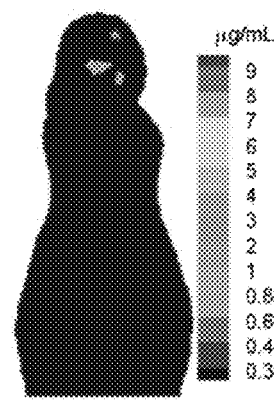
FIG. 10A shows true nanophosphor concentration distribution in a mouse model.
Figure 10B:
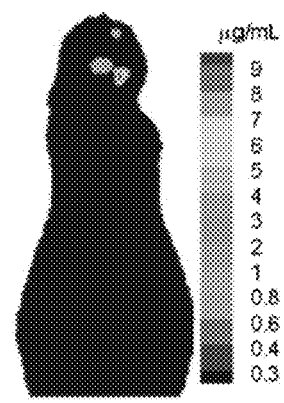
FIG. 10B shows true nanophosphor concentration distribution in a mouse model.
Figure 10C:
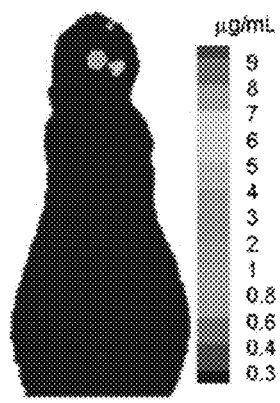
FIG. 10C shows true nanophosphor concentration distribution in a mouse model.
Figure 10D:
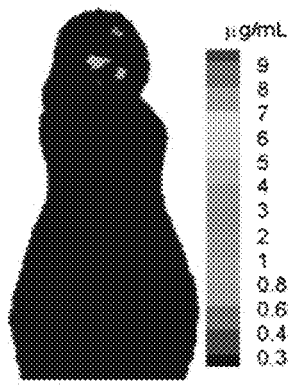
FIG. 10D shows reconstructed nanophosphor concentration distribution in a mouse model.
Figure 10E:
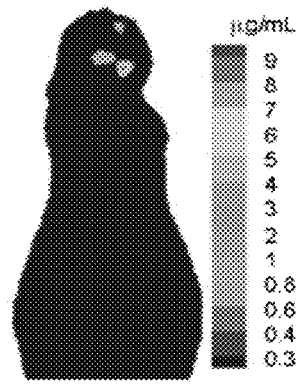
FIG. 10E shows reconstructed nanophosphor concentration distribution in a mouse model.
Figure 10F:
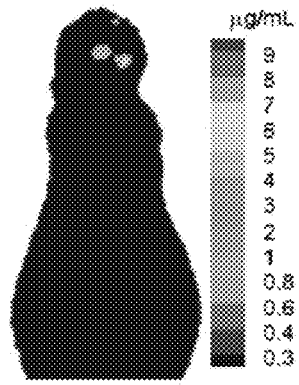
FIG. 10F shows reconstructed nanophosphor concentration distribution in a mouse model.

FIGS. 10A-10F compare the true and reconstructed nanophosphor clusters, showing the quantification accuracy of the reconstruction method. FIG. 10A shows the true nanophosphor distribution at z=11.3 mm; FIG. 10B shows the true nanophosphor distribution at z=12 mm; and FIG. 10C shows the true nanophosphor distribution at z=12.7 mm. FIG. 10D shows the reconstructed nanophosphor distribution at z=11.3 mm; FIG. 10E shows the reconstructed nanophosphor distribution at z=12 mm; and FIG. 10F shows the reconstructed nanophosphor distribution at z=12.7 mm. With a minimal separation of 50 µm among the three subregions, the reconstructed images suggest that the nanophosphor-labeled features can be accurately imaged. The numerical simulation also indicates that the minimal detectable concentration of nanophosphors is about 0.3 µg/ml, whereas the highest nanophosphor concentration in this example was 10 µg/ml.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

Alexandrakis, G. et al., "Tomographic bioluminescence imaging by use of a combined optical-PET (OPET) system: a computer simulation feasibility study," *Physics in Medicine and Biology*, vol. 50, pp. 4225-4241, September 2005.

Alivisatos, P. "The use of nanocrystals in biological detection," *Nat Biotechnol* 22(1), 47-52 (2004).

Arridge, S. R. et al., "A finite element approach for modeling photon transport in tissue," *Med. Phys.* 20, 299-309 (1993).

Basavaraju, N. et al., "Red persistent luminescence in $MgGa_2O_4:Cr3+$: a new phosphor for in vivo imaging," *J. Phys. D* 46, 375401 (2013).

Brannon-Peppas, L. et al., "Nanoparticle and targeted systems for cancer therapy," *Advanced Drug Delivery Reviews*, vol. 56, pp. 1649-1659, September 2004.

Cai, X. et al., "Photoacoustic Microscopy in Tissue Engineering," *Mater Today (Kidlington)* 16(3), 67-77 (2013).

Candes, E. J. et al., "Robust uncertainty principles: Exact signal reconstruction from highly incomplete frequency information," *IEEE Transactions on Information Theory*, vol. 52, pp. 489-509, February 2006.

Carpenter, C. M. et al., "Hybrid x-ray/optical luminescence imaging: characterization of experimental conditions," *Med. Phys.* 37, 4011-4018 (2010).

Chang, M. et al., "A Few-view Reweighted Sparsity Hunting (FRESH) Method for CT Image Reconstruction," *Journal of X-ray Science and Technology* 21(2), 161-176 (2013).

Chen, D. et al., "Cone beam x-ray luminescence computed tomography: a feasibility study," *Med. Phys.* 40, 031111 (2013).

Chen, J. et al., "Mesh-based Monte Carlo method in time-domain widefield fluorescence molecular tomography," *J. Biomed. Opt.* 17(10), 106009 (2012).

Chien, K. R. "Regenerative medicine and human models of human disease," *Nature* 453 (7193), 302-305 (2008).

Cong, A. et al., "Differential evolution approach for regularized bioluminescence tomography," *IEEE Transactions on Biomed. Eng.* 57, 2229-2238 (2010).

Cong, W. et al., "Practical reconstruction method for bioluminescence tomography," *Opt. Express* 13(18), 6756-6771 (2005).

Cong, W. et al., "Spectrally resolving and scattering compensated x-ray luminescence/fluorescence computed tomography," *J. Biomed. Opt.* 16(6), 066014 (2011).

Cong, W. et al., "Stored Luminescence Computed Tomography," *International Journal of Engineering and Innovative Technology*, Accepted (2013).

Cong, W. et al., "X-ray micro-modulated luminescence tomography (XMLT)," *Opt. Express* 22(5), 5572-5580 (2014).

David, C. et al., "Nanofocusing of hard X-ray free electron laser pulses using diamond based Fresnel zone plates," *Sci Rep* 1, 57 (2011).

Donoho, D. L. et al., "Compressed sensing," *IEEE Transactions on Information Theory*, vol. 52, pp. 1289-1306, April 2006.

Fass, L. "Imaging and cancer: a review," *Mol. Oncol.* 2(2), 115-52 (2008).

Gao, X. H. et al., "In vivo cancer targeting and imaging with semiconductor quantum dots," *Nature Biotechnology* 22(8), 969-976 (2004).

Goy, A. S. et al., "Multiple contrast metrics from the measurements of a digital confocal microscope," *Biomed Opt Express* 4(7), 1091-1103 (2013).

Haskell, R. C. et al., "Boundary conditions for the diffusion equation in radiative transfer," *J Opt Soc Am A* 11 (10), 2727-2741 (1994).

Huang, B. et al., "Three-dimensional super-resolution imaging by stochastic optical reconstruction microscopy," *Science* 319(5864), 810-813 (2008).

Ishimaru, A. *"Wave propagation and scattering in random media,"* Oxford: Oxford Unversity Press, 1997.

Jalili, N. et al., "A review of atomic force microscopy imaging systems: application to molecular metrology and biological sciences," *Mechatronics* 14(8), 907-945 (2004).

Kim, A. D. et al., "Light propagation in biological tissue," *J. Opt. Soc. Am. A* 20(1), 92-98 (2003).

Kim, S. J. et al., "An Interior-Point Method for Large-Scale l1-Regularized Least Squares," *IEEE Journal of Selected Topics in Signal Processing*, vol. 1, 606-617, December 2007.

Klose, A. D. et al., "Light transport in biological tissue based on the simplified spherical harmonics equations," *Journal of Computational Physics* 220(1), 441-470 (2006).

Liemert, A. et al., "Analytical Green's function of the radiative transfer radiance for the infinite medium," *Phys Rev E* 83(3), 036605 (2011).

Liu, F. et al., "Photostimulated near-infrared persistent luminescence as a new optical read-out from Cr3+-doped LiGa5O8," *Sci. Rep.* 3, 1554 (2013).

Ma, C. M. et al., "AAPM protocol for 40-300 kV x-ray beam dosimetry in radiotherapy and radiobiology," *Medical Physics*, vol. 28, pp. 868-93, June 2001.

Milstein, A. B. et al., "Fluorescence optical diffusion tomography," *Applied Optics*, vol. 42, pp. 3081-3094, June 2003.

Nie, S. M. et al., "Nanotechnology applications in cancer," *Annual Review of Biomedical Engineering* 9, 257-288 (2007).

Ntziachristos, V. et al., "Experimental three-dimensional fluorescence reconstruction of diffuse media using a normalized Born approximation," *Optics Letters*, vol. 26, pp. 893-895, December 2001.

Ntziachristos, V. et al., "Looking and listening to light: the evolution of whole-body photonic imaging," *Nat. Biotechnol.* 23(3), 313-320 (2005).

Pan, Z. et al., "Sunlight-activated long-persistent luminescence in the near-infrared from Cr3+-doped zinc gallogermanates," *Nat. Mater.* 11(1), 58-63 (2012).

Panasyuk, G. Y. et al., "Superresolution and corrections to the diffusion approximation in optical tomography," *Appl. Phys. Lett.* 87(10), 101111 (2005).

Perrault, S. D. et al., "In vivo assembly of nanoparticle components to improve targeted cancer imaging," *Proc Natl Acad Sci USA* 107(25), 11194-11199 (2010).

Pong, W. T. et al., "A review and outlook for an anomaly of scanning tunneling microscopy (STM): Superlattices on graphite," *Journal of Physics D-Applied Physics* 38(21), R329-R355 (2005).

Prahl, S. A. "Optical properties spectra," *Oregon Medical Laser Clinic*, http://omlc.ogi.edu/spectra/index.html, 2001.

Pratx, G. et al., "Tomographic molecular imaging of x-ray-excitable nanoparticles," *Opt. Lett.* 35, 3345-3347 (2010).

Pratx, G. et al., "X-ray luminescence computed tomography via selective excitation: a feasibility study," *IEEE Trans. Med. Imaging* 29, 1992-1999 (2010).

Qian, X. M. et al., "In vivo tumor targeting and spectroscopic detection with surface-enhanced Raman nanoparticle tags," *Nat. Biotechnol.* 26(1), 83-90 (2008).

Ricci, C. et al., "Cancer tissue engineering: new perspectives in understanding the biology of solid tumors: A critical review," *OA Tissue Engineering* 1(1), 4 (2013).

Rice, B. W. et al., "In vivo imaging of light-emitting probes," *Journal of Biomedical Optics* 6(4), 432-440 (2001).

Schweiger, M. et al., "The finite element method for the propagation of light in scattering media: boundary and source conditions," *Med. Phys.* 22(11), 1779-1792 (1995).

Shin, S. J. et al., "Targeted nanoparticles in imaging: paving the way for personalized medicine in the battle against cancer," *Integr Biol (Camb)* 5(1), 29-42 (2013).

Solanki, A. et al., "Nanotechnology for regenerative medicine: nanomaterials for stem cell imaging," *Nanomedicine (Lond)* 3(4), 567-578 (2008).

Sunderland, C. J. et al., "Targeted nanoparticles for detecting and treating cancer," *Drug Dev. Res.* 67(1), 70-93 (2006).

Timpson, P. et al., "Imaging molecular dynamics in vivo—from cell biology to animal models," *J Cell Sci* 124 (17), 2877-2890 (2011).

Vila-Comamala, J. et al., "Zone-doubled Fresnel zone plates for high-resolution hard X-ray full-field transmission microscopy," *J Synchrotron Radiat* 19(5), 705-709 (2012).

Wang, G. et al., "In vivo mouse studies with bioluminescence tomography," *Opt. Express* 14, 7801-7809 (2006).

Wang, G. et al., "Uniqueness theorems in bioluminescence tomography," *Med. Phys.* 31, 2289-2299 (2004).

Wang, L. V. "Multiscale photoacoustic microscopy and computed tomography," *Nat Photonics* 3(9), 503-509 (2009).

Weersink, R. A. et al., "Improving superficial target delineation in radiation therapy with endoscopic tracking and registration," *Medical Physics, vol.* 38, pp. 6458-68, December 2011.

Weinand, C. et al., "Conditions affecting cell seeding onto three-dimensional scaffolds for cellular-based biodegradable implants," *J Biomed Mater Res B Appl Biomater* 91(1), 80-87 (2009).

Weissleder, R. et al., "Shedding light onto live molecular targets," *Nat. Med.* 9(1), 123-128 (2003).

Welch, J. et al., *Optical and Thermal Response of Laser-Irradiated Tissue* (Plenum, 1995).

Withers, P. J., "X-ray nanotomography," *Mater. Today* 10(12), 26-34 (2007).

Wongsrichanalai, C. et al., "A review of malaria diagnostic tools: Microscopy and rapid diagnostic test (RDT)," *American Journal of Tropical Medicine and Hygiene* 77(6), 119-127 (2007).

Wu, S. et al., "Hard-X-ray Zone Plates: Recent Progress," *Materials* 5(10), 1752-1773 (2012).

What is claimed is:

1. An imaging method, comprising:
   using an X-ray source and an X-ray focusing component to excite nanoparticles in a distribution pattern within a sample that is to be imaged, wherein the excitation causes the nanoparticles to store energy provided by the X-ray source;
   stimulating the sample with infrared or near-infrared (NIR) light from at least one light source, wherein stimulating the sample with infrared or near infrared light causes the nanoparticles to release the stored energy as emitted luminescence light; acquiring tomographic data of the sample by capturing the luminescence light emitted by the nanoparticles using at least one camera facing the sample; and
   reconstructing a tomographic image of the sample from the acquired tomographic data.

2. The imaging method according to claim 1, wherein the sample is a biological sample.

3. The imaging method according to claim 1, wherein the nanoparticles comprise nanophosphors.

4. The imaging method according to claim 1, wherein the nanoparticles comprise $LiGa_5O_8:Cr^{3+}$, $MgGa_2O_4:Cr^{3+}$, or both.

5. The imaging method according to claim 1, wherein the at least one camera is a charge coupled device (CCD) camera.

6. The imaging method according to claim 1, wherein the sample, the X-ray source, the X-ray focusing component, the at least one camera, and the at least one light source are all contained within an optically opaque cover during the steps of using the X-ray source and the X-ray focusing component to excite the nanoparticles in the distribution pattern within the sample and acquiring the tomographic data of the sample.

7. The imaging method according to claim 1, wherein the luminescence light emitted by the nanoparticles is captured using two cameras, and wherein, during the step of acquiring the tomographic data of the sample, the sample is positioned between the two cameras.

8. The imaging method according to claim 1, wherein capturing the luminescence light emitted by the nanoparticles comprises using the at least one camera and a mirror imaging device comprising two mirrors, wherein, during the step of acquiring the tomographic data of the sample, the sample is positioned between the at least one camera and the mirror imaging device, and wherein, during the step of acquiring the tomographic data of the sample, the two mirrors of the mirror imaging device are positioned such that the luminescence light from the sample is reflected off the mirrors to the at least one camera.

9. The imaging method according to claim 1, wherein using the X-ray source and the X-ray focusing component to excite nanoparticles in the distribution pattern within the sample comprises focusing the X-ray source onto a target area of the sample and activating the X-ray source.

10. The imaging method according to claim 1, wherein stimulating the sample comprises stimulating the sample with near-infrared (NIR) light and the at least one light source comprises at least one NIR light source.

11. The imaging method according to claim 1, wherein the sample is a biological sample,
    wherein the nanoparticles comprise nanophosphors,
    wherein the at least one camera is an EMCCD camera,
    wherein stimulating the sample comprises stimulating the sample with NIR light and the at least one light source comprises at least one NIR light source, and
    wherein, during the steps of using the X-ray source and the X-ray focusing component to excite the nanoparticles in the distribution pattern within the sample and acquiring the tomographic data of the sample, the sample, the X-ray source, the X-ray focusing component, the at least one camera, and the at least one light source are all contained within an optically opaque cover.

12. The imaging method according to claim 11, wherein the nanoparticles comprise $LiGa_5O_8:Cr^{3+}$, $MgGa_2O_4:Cr^{3+}$, or both.

13. The imaging method according to claim 1, wherein the X-ray focusing component is a polycapillary lens or a zone plate.

* * * * *